US012668778B2

(12) United States Patent
Zhang et al.

(10) Patent No.: US 12,668,778 B2
(45) Date of Patent: Jun. 30, 2026

(54) METHOD FOR EXPANSION OF DOUBLE NEGATIVE REGULATORY T CELLS

(71) Applicant: UNIVERSITY HEALTH NETWORK, Toronto (CA)

(72) Inventors: Li Zhang, Toronto (CA); Paulina Achita, Mississauga (CA); Jongbok Lee, Toronto (CA); Dalam Ly, Toronto (CA); Dzana Dervovic, Toronto (CA)

(73) Assignee: UNIVERSITY HEALTH NETWORK, Toronto (CA)

( * ) Notice: Subject to any disclaimer, the term of this patent is extended or adjusted under 35 U.S.C. 154(b) by 692 days.

(21) Appl. No.: 18/146,142

(22) Filed: Dec. 23, 2022

(65) Prior Publication Data

US 2023/0128394 A1 Apr. 27, 2023

Related U.S. Application Data

(62) Division of application No. 15/573,379, filed as application No. PCT/CA2016/000136 on May 11, 2016, now Pat. No. 11,534,460.

(60) Provisional application No. 62/237,050, filed on Oct. 5, 2015, provisional application No. 62/159,561, filed on May 11, 2015.

(51) Int. Cl.
| | |
|---|---|
| *C12N 5/0783* | (2010.01) |
| *A61K 40/11* | (2025.01) |
| *A61K 40/22* | (2025.01) |
| *A61K 40/41* | (2025.01) |
| *A61K 40/42* | (2025.01) |
| *A61P 35/00* | (2006.01) |
| *A61K 40/50* | (2025.01) |

(52) U.S. Cl.
CPC ............ *C12N 5/0637* (2013.01); *A61K 40/11* (2025.01); *A61K 40/22* (2025.01); *A61K 40/418* (2025.01); *A61K 40/42* (2025.01); *A61P 35/00* (2018.01); *A61K 40/50* (2025.01); *A61K 2239/31* (2023.05); *A61K 2239/38* (2023.05); *A61K 2239/48* (2023.05); *C12N 2501/51* (2013.01); *C12N 2501/515* (2013.01); *C12N 2501/999* (2013.01)

(58) Field of Classification Search
CPC ...................... C12N 5/0637; C12N 2501/515; A61K 40/11; A61K 40/22; A61K 40/418; A61K 2239/48
See application file for complete search history.

(56) References Cited

U.S. PATENT DOCUMENTS

| | | |
|---|---|---|
| 7,638,326 B2 | 12/2009 | June |
| 9,018,004 B2 | 4/2015 | Zhang et al. |
| 9,907,820 B2 | 3/2018 | Cooper et al. |
| 2014/0044687 A1 | 2/2014 | Forte et al. |
| 2014/0212446 A1 | 7/2014 | Riley et al. |

FOREIGN PATENT DOCUMENTS

| | | |
|---|---|---|
| WO | WO 2005/118788 | 12/2005 |
| WO | WO 2007/056854 | 5/2007 |
| WO | WO 2010/090995 | 8/2010 |

OTHER PUBLICATIONS

Thomson et al. Double-Negative Regulatory T Cells: Non-conventional Regulators. Immunologic Research 2006;34/1-2:163-177 (Year: 2006).*
Hillhouse et al. Immunoregulatory CD4-CD8- Tcells as a potential therapeutic tool for transplantation, autoimmunity, and cancer. Frontier in Immunology. vol. 4, article 6, p. 1-10 (Year: 2013).*
Demarco. Graft vs. host disease: 6 things to know about this stem cell transplant side effect. Stem cell transplant side effect: Graft vs. host disease (GVHD) | MD Anderson Cancer Center. p. 1-5 (Year: 2021).*
Dobson et al. Editorial: Preventing multiple sclerosis. Front. Neurol. 13:982411. p. 1-3 (Year: 2022).*
Kim et al. Regulatory CD4– CD8– Double Negative T Cells. In: Cuturi, M., Anegon, I. (eds) Suppression and Regulation of Immune Responses. Methods in Molecular Biology, vol. 677. Humana Press, Totowa, NJ. https://doi.org/10.1007/978-1-60761-869-0_6, p. 100-113 (Year: 2010).*
List of Autoimmune Diseases. Enhancing NIH Research on Auto-immune Disease. NCBI Bookshelf. p. 1-6 (Year: 2022).*
Patel et al. PI3K/AKT Signaling and Systemic Autoimmunity. Immunologic Research 2005;31/1:47-55 (Year: 2005).*
Klumpen et al. Inhibitors of mTOR. The Oncologist 2010;15:1262-1269 (Year: 2010).*
Autoimmune Disease. downloaded from https://larkinhealth.com/en/treatments-services/rheumatology/autoimmune-disease/, p. 1-5 (Year: 2022).*
Allgauer et al., "IL-7 Abrogates the Immunosuppressive Function of Human Double-Negative T Cells by Activating Akt/mTOR Signaling," Journal of Immunology, 195(7); 3139-3148, 2015.
Araki et al., "Allogeneic Hematopoietic Cell Transplantation for Acute Myeloid Leukemia: Time to Move Toward a Minimal Residual Disease-Based Definition of Complete Remission?" Journal of Clinical Oncology: Official Journal of the American Society of Clinical Oncology, 34; 329-336, 2016.
Attridge et al., "IL-21 inhibits T cell IL-2 production and impairs Treg homeostasis" Blood 2012, 119(20), 4656-4664.
Barrett & Childs, "Non-Myeloablative Stem Cell Transplants," British Journal of Haematology, 11; 6-17, 2000.
Brissot et al., "Which Acute Myeloid Leukemia Patients Should Be Offered Transplantation?" Semin Hemtol, 52, 223-231, 2015.
Butler and Hirano, "Human cell-based artificial antigen-presenting cells for cancer immunotherapy," Immunol. Rev., 257(1): 191-209, 2014.

(Continued)

*Primary Examiner* — Taeyoon Kim
(74) *Attorney, Agent, or Firm* — Norton Rose Fulbright US LLP

(57) ABSTRACT

There is provided herein a method for expanding human CD4⁻CD8⁻ regulatory T cells (DN Tregs) from a population of cells comprising DN Tregs, comprising: culturing the population of cells with artificial antigen presenting cells (APCs), preferably the DN Tregs are αβ-TCR⁺CD56⁻ or alternatively γδ-TCR+.

23 Claims, 10 Drawing Sheets

(56) References Cited

OTHER PUBLICATIONS

Butler et al., "Ex Vivo Expansion of Human CD8+ T Cells Using Autologous CD4+ T Cell Help," PLOS One, 7(1); e30229, 2012.

Champlin et al., "Harnessing Graft-Versus-Malignancy: Non-Myeloablative Prepartive Regimens for Allogeneic Haematopoietic Transplantation, An Evolving Strategy for Adoptive Immunotherapy," British Journal of Hematology, 111; 18-29, 2000.

Chantry et al., "Long-Term Outcomes of Myeloablation and Autologous Tranplantation of Relapsed Acute Myeloid Leukemia in Second Remission: A British Society of Blood and Marrow Transplantation Registry Study. Biology of Blood and Marrow Transplantation," Journal of the American Society for Blood and Marrow Transplantation, 12; 1310-1317, 2006.

Chen et al., "Both Infiltrating Regulatory T Cells and Insufficient Antigen Presentation Are Involved in Long-Term Cardiac Xenograft Survival," Journal of Immunology, 179(3); 1542-1548, 2007.

Chen et al., "Donor Lymphocyte Infusion Induces Long-Term Donor-Specific Cardia Xenograft Survival Through Activation of Recipient Double-Negative Regulatory T Cells," Journal of Immunology, 175(5); 3409-3416, 2005.

Chen et al., "Infusion of In Vitro-Generated Dn T Regulatory Cells Induces Permanent Cardiac Allograft Survival in Mice," Transplant Proceedings, 35(7); 2479-2480, 2003.

Choi et al., "4-1BB-dependent inhibition of immunosuppression by activated CD4⁺CD25⁺ T cells," Journal of Leukocyte Biology, 75:785-791, 2004.

Cornelissen et al., "Results of a HOVON/SAKK Donor Versus No. Donor Analysis of Myeloablative HLA-Identical Stem Cell Transplantation in First Remission Acute Myeloid Leukemia in Young and Middle-Aged Adults: Benefits for Whom?," Blood, 109; 3658-3666, 2007.

Cornelissen et al., "The European LeukemiaNet AML Working Party Consensus Statement on Allogeneic HSCT for Patients with AML in Remission: An Integrated-Risk Adapted Approach," Nature Reviews Clinical Oncology, 9; 579-590, 2012.

Covassin et al., "Human Peripheral Blood CD4 T Cell-Engrafted Non-Obese Diabetic-Scid IL2Rgamma(null) H2-Ab1 (tm1Gru) Tg (Human Leucocyte Antigen D-Related 4) Mice: A Mouse Model of Human Allogeneic Graft-Versus-Host Disease," Clinical and Experimental Immunology, 166; 269-280, 2011.

Curiel et al., Tregs, and Rethinking Cancer Immunotherapy, Journal of Clinical Investigation, 115(5); 1167-1174, 2007.

Dienstmann et al., "Picking the Point of Inhibition: A Comparative Review of P13K/AKT/mTOR Pathway Inhibitors," Molecular Cancer Therapeutics, 13(5); 1021-1031, 2014.

Edinger et al., "CD4+CD25+ Regulatory T Cells Preserve Graft-Versus-Tumor Activity While Inhibiting Graft-Versus-Host Disease After Bone Marrow Transplantation," Nature Medicine 9,; 1144-1150, 2003.

Efimova et al., "Induction of granzyme B expression in T-cell receptor/CD28-stimulated human regulatory T cells is suppressed by inhibitors of the PI3K-mTOR pathway," BMC Immun., 10:59, pp. 1-13, 2009.

Fischer et al., "Isolation and Characterization of Human Antigen-Specific TCR Alpha Beta+CD4(−)CD8−Double-Negative Regulatory T Cells," Blood, 105(7); 2828-2835, 2005.

Fontaine et al., "Adoptive Transfer of Minor Histocompatibility Antigen-Specific T Lymphocytes Eradicates Leukemia Cells Without Causing Graft-Versus-Host Disease," Nature Medicine, 7; 789-794, 2001.

Ford et al., "Peptide-Activated Double-Negative T Cells Can Prevent Autoimmune Type-1 Diabetes Development," European Journal of Immunology, 37(8); 2234-2241, 2007.

Ford et al., "The Immune Regulatory Function of Lymphoproliferative Double Negative T Cells in Vitro and in Vivo," Journal of Experimental Medicine, 196(2); 261-267, 2002.

Fujii et al., "Humanized Chronic Graft-Versus-Host Disease in NOD-SCID IL2RGamme-/- (NSG) Mice with G-CSF-Mobilized Peripheral Blood Mononuclear Cells Following Cyclophosphamide and Total Body Irradiation," PLoS One, 10,; e0133216, 2015.

Golovina et al., "CD28 costimulation is essential for human T regulatory expansion and function," J. Immunol., 181:2855-2868, 2008.

Gooley et al., "Reduced Mortality After Allogeneic Hemtopoietic-Cell Transplantation," New England Journal of Medicine, 363; 2091-2101, 2010.

Gowda et al., "Differential effects of IL-2 and IL-21 on expansion of the CD4+ CD25+ Foxp3+ T regulatory cells with redundant roles in natural killer cell mediated antibody dependent cellular cytotoxicity in chronic lymphocytic leukemia," MAbs, 2(1):35-41, 2010.

Hashmi et al., "Interleukin-21: updated review of Phase I and II clinical trials in metastatic renal cell carcinoma, metastatic melanoma and relapsed/refractory indolent non-Hodgkin's lymphoma" Expert Opinion on Biological Therapy 2010, 10(5), 807-817.

He et al., "Donor Double-Negative Treg Promote Allogeneic Mixed Chimerism and Tolerance," European Journal of Immunology, 37(12); 3455-3466, 2007.

He et al., "Identification of a novel splice variant of human PD-L1 mRNA encoding an isoform-lacking Igv-like domain," Acta Pharm. Sin., 26(4):462-468, 2005.

Hillhouse & Lesage et al., "A Comprehensive Review of the Phenotype and Function of Antigen-Specific Immunoregulatory Double NegativeT Cells," Journal of Autoimmunity, 40; 58-65, 2013.

Hippen et al., "Massive Ex Vivo Expansion of Human Natural Regulatory T Cells (T(regs)) with Minimal Loss of in Vivo Functional Activity," Science Translational Medicine, 3(83); 83ra41, 2011.

Horowitz et al., "Graft-Versus-Leukemia Reactions After Bone Marrow Transplantation," Blood, 75; 555-562, 1990.

International Search Report and Written Opinion Issued in Corresponding PCT Application No. PCT/CA2016/000136, mailed Aug. 4, 2016.

Johnson et al., "A Chronic Need for IL-21" Science 2009, 324, 1525-1526.

Juvet et al., "Autocrine IFNgamma Controls the Regulatory Function of Lymphoproliferative Double Negative T Cells," PLoSOne, 7(10); e47732, 2012.

Keir et al., "Programmed death-1 (PD-1):PD-ligand 1 interactions inhibit TCR-mediated positive selection of thymocytes," J. Immuno., 175(11):7372-7379, 2005.

Kim-Schulze et al., "Local IL-21 Promotes the Therapeutic Activity of Effector T cells by Decreasing Regulatory T Cells Within the Tumor Microenvironment" Molecular Therapy 2009, 17(2), 380-388.

Knight et al., "Discovery of GSK2126458, a Highly Potent Inhibitor of PI3K and the Mammalian Target of Rapamycin," ACS Med. Chem., 1(1):39-43, 2010.

Lee et al., "Expression Profiling of Murine Double-Negative Regulatory T Cells Suggest Mechanisms for Prolonged Cardiac Allograft Survival," Journal of Immunology, 174(8); 4535-4544, 2005.

McIver et al., "Double-Negative Regulatory T Cells Induce Alloteolerance When Expanded After Allogeneic Haematopoietic Stem Cell Transplantation," British Journal of Haematology, 141; 170-178, 2008.

McMurchy et al., "Moving to Tolerance: Clinical Application of T Regulatory Cells," Seminars in Immunology, 23(4); 304-313, 2011.

Merims et al., "Anti-Leukemia Effect of Ex Vivo Expanded DNT Cells from AML Patients: A Potential Novel Autologous T-Cell Adoptive Immunotherapy," Leukemia, 25(9); 1415-1422, 2011.

Montero et al., "T-Cell Depleted Peripheral Blood Stem Cell Allotransplatation with T-Cell Add-Back for Patients with Hematological Malignancies: Effect of Chronic GVHD on Outcome," Biology of Blood Marrow Transplant, 12; 1318-1325, 2006.

Moroz et al., "IL-21 Enhances and Sustains CD8+ T Cell Responses to Achieve Durable Tumor Immunity: Comparative Evaluation of IL-2, IL-15, and IL-21" J Immunol 2004, 173, 900-909.

Priatel & Utting, "TCR/Self-Antigen Interactions Drive Double-Negative T Cell Peripheral Expansion and Differentiation into Suppressor Cells," Journal of Immunology, 167(11); 6188-6194, 2001.

(56)        References Cited

OTHER PUBLICATIONS

Sakaguchi et al., Regulatory T Cells and Immune Tolerance,: Cell, 133(5); 775-787, 2008.

Schmid et al., "Outcome of Patients with Distinct Molecular Gentypes and Cytogenetically Normal AML After Allogeneic Transplantation," Blood, 126; 2062-2069, 2015.

Shan et al., "The Effects of Rapamycin on Regulatory T Cells: Its Potential Time-Dependent Role in Inducing Transplant Intolerance," Immunology Letters, 162 (1 Pt A); 74-86, 2014.

Sprangers et al., "Experimental and Clinical Approaches for Optimization of the Graft-Versus-Leukemia Effect," Nat Clin Pract Oncol, 4; 404-414, 2007.

Stonehouse et al., "Molecular characterization of U937-dependent T-cell co-stimulation," Immunology, 96(1):35-47, 1999.

Tang et al., "T-Cell Therapy in Transplantation: Moving to the Clinic," Cold Springs Harbor Perspectives in Medicine, 2013.

Thomson et al., "Lentivirally transduced recipient-derived dendritic cells serve to ex vivo expand functional FcRgamma-sufficient double-negative regulatory T cells," Mol. Ther., 15(4):818-824, 2007.

Toda & Piccirillo, "Development and Function of Naturally Occurring CD4+CD25+ Regulatory T Cells," Journal of Leukocyte Biology, 80(3); 458-470, 2006.

Trzonkowski et al., Treatment of Graft-vs-Host Disease with Naturally Occurring T Regulatory Cells, BioDrugs, 27(6); 605-614, 2013.

Van den Brink et al., "Relapse After Allogeneic Hematopoietic Cell Therapy," Biol Blood Marrow Transplant, 16; S138-145, 2010.

Van Rijn et al., "A New Xenograft Model for Graft-Versus-Host Disease by Intravenous Transfer of Human Peripheral Blood Mononuclear Cells in RAG2-/-gammac-/-Double-Mutant Mice," Blood, 102; 2522-2531, 2003.

Veiga-Parga et al., "Role of Regulatory T Cells During Virus Infection," Immunology Review, 255(1); 182-196, 2013.

Vincent et al., "Next-Generation leukemia Immunotherapy," Blood, 118; 2951-2959, 2011.

Voelkl et al., "Characterization of the Immunoregulatory Function of Human TCR-Alphabeta+ CD4−CD8− Double-Negative T Cells," European Journal of Immunology, 41(3); 739-748, 2011.

Von Boehmer, "Therapeutic Opportunities for Manipulating Treg Cells in Autoimmunity and Cancer," Nature Reviews Drug Discovery, 12; 51-63, 2013.

Vyas et al., "Reprint of: Allogeneic Hematopoietic Cell Transplantation for Acute Myeloid Leukemia," Biology of Blood and Marrow Transplant, 21; S3-10, 2015.

Weiden et al., "Antileukemia Effect of Graft-Versus-Host Disease in Human Recipients of Allogeneic-Marrow Grafts," The New England Journal of Medicine, 300; 1068-1073, 1979.

Wood et al., "Regulatory Immune Cells in Transplantation," Nature Reviews Immunology, 12(6); 417-430, 2012.

Yanaba et al., "The Development and Function of Regulatory B Cells Expressing IL-10(B10 Cells) Requires Antigen Receptor Diversity and TLR Signals," Journal of Immunology, 182(12); 7459-7472, 2009.

Ye et al., "Characterization of CD3+CD4−CD8− (Double Negative) T Cells Reconstitution in Patients Following Hematopoietic Stem-Cell Transplantation," Transplant Immunology, 25; 180-186, 2011.

Young et al., "Antitumor Activity Mediated by Double-Negative T Cells," Cancer Research, 63; 8014-8021, 2003.

Young et al., "CD4−CD8− Regulatory T Cells Implicated in Preventing Graft-Versus-Host and Promoting Graft-Versus-Leukemia Responses," Transplantation Proceedings, 33; 1762-1763, 2001.

Young et al., "Inhibition of Graft-Versus-Host Disease by Double-Negative Regulatory T Cells," Journal of Immunology, 171; 134-141, 2003.

Zhang et al., "Identification of a Previously Unknown Antigen-Specific Regulatory T Cell Its Mechanism of Suppression," Nature Medicine, 6; 782-789, 2000.

Zhang et al., "New Differentiation Pathway for Double-Negative Regulatory T Cells that Regulates the Magnitude of Immune Responses," Blood, 109(9); 4071-4079, 2007.

Zheng et al., "The 4-1BB costimulation augments the proliferation of CD4+CD25+ regulatory T cells," J. Immunol., 173(4):2428-2434, 2004.

* cited by examiner

A

B

A

B

A

B

METHOD FOR EXPANSION OF DOUBLE NEGATIVE REGULATORY T CELLS

RELATED APPLICATIONS

This application is a divisional application of U.S. patent application Ser. No. 15/573,379, filed Nov. 10, 2017, which is a national phase application under 35 U.S.C. § 371 of International Application No. PCT/CA2016/000136, filed May 11, 2016, which claims priority to U.S. Provisional Patent Application Nos. 62/159,561 and 62/237,050, filed on May 11, 2015 and Oct. 5, 2015, respectively, each of which are incorporated herein by reference in their entirety.

FIELD

The present invention relates to regulatory T cells, and in particular methods of expanding the double negative subset of regulatory T cells.

BACKGROUND

Compelling evidence has shown the importance of regulatory T cells (Tregs) in controlling various diseases including autoimmune diseases, allograft rejection, graft vs. host disease (GVHD), infections and cancer[1-7,9]. Tregs consist of many distinct subsets, although naturally occurring CD4$^+$CD25$^+$Foxp3$^+$ Tregs (nTregs) are the most extensively studied[8,9]. Applicant refers also to its issued U.S. Pat. No. 9,018,004 for expanding double negative T cells.

Applicant previously identified and characterized another subset of Tregs which express αβ-TCR but not CD4, CD8, or NK cell marker NK1.1 (in mice) or CD56 (in humans), and termed double negative regulatory T cells, or DN Tregs in short[1]. DN Tregs comprise 1% of mature CD3$^+$ T cells in rodents[11] and humans[10]. It has been demonstrated that adoptive transfer of DN Tregs can establish and maintain donor-specific tolerance to allogeneic islet, skin and heart, as well as xenogeneic heart grafts[11-17]. DN Tregs can also attenuate allogeneic CD4$^+$ and CD8$^+$ T cell-mediated GVHD[18-21], and control autoimmune diabetes, lymphoproliferative syndrome and infection[12,22-24]. Human DN Tregs have similar cell surface marker expression and produce similar cytokines as their murine counterparts, and can also suppress Ag-specific immune responses in vitro[10,25]. In addition, a higher frequency of DN Tregs in patient blood after hematopoietic stem cell transplantation correlates with mild GVHD[26,27]. Collectively, these findings demonstrate that DN Tregs can control the development and pathogenesis of various diseases by suppressing antigen-specific immune responses.

Given that numerous pre-clinical studies have demonstrated the importance of Tregs in controlling various diseases, many attempts have been made to produce large numbers of human Tregs for clinical use. It is now possible to produce therapeutic numbers of anti-CD3-activated polyclonal nTregs for clinical trials[28]. It has been shown that human DN Tregs can be generated by stimulation with allogeneic monocyte-derived dendritic cells[10]. However, the number of human DN Tregs generated in this way is very limited.

SUMMARY

In an aspect, there is provided a method for expanding human CD4$^-$CD8$^-$ regulatory T cells (DN Tregs) from a population of cells comprising DN Tregs, comprising: culturing the population of cells with antigen presenting cells (APCs), preferably the DN Tregs are CD56$^-$, αβ-TCR$^+$, γδ-TCR+, or combinations thereof.

In an aspect, there is provided a population of DN Tregs obtained by the methods described herein.

In an aspect, there is provided a use of DN Tregs for the treatment of cancer, preferably leukemia or lung cancer.

In an aspect, there is provided a use of DN Tregs in the preparation of a medicament for the treatment of cancer, preferably leukemia or lung cancer.

In an aspect, there is provided a method of treating cancer in a subject, preferably leukemia or lung cancer, comprising administering to the subject a therapeutically effective amount of DN Tregs.

In an aspect, there is provided a use of DN Tregs for the treatment or prevention of allograft rejection, GVHD, or an autoimmune disease.

In an aspect, there is provided a use of DN Tregs in the preparation of a medicament for the treatment or prevention of allograft rejection, GVHD, or autoimmune diseases.

In an aspect, there is provided a method of treating or preventing allograft rejection, GVHD, or an autoimmune disease, comprising administering to the subject a therapeutically effective amount of DN Tregs.

BRIEF DESCRIPTION OF THE DRAWINGS

Embodiments of the present disclosure will now be described, by way of example only, with reference to the attached Figures.

FIG. 1 shows isolation and expansion of DN Tregs. (A) DN Tregs were enriched by staining PBMCs with CD4-FITC, CD8-FITC, CD56-FITC, TCRγδ-FITC Abs and depleting the stained cells using anti-FITC magnetic beads and MACS technology. Representative flow cytometry histograms of pre- and post-sort are shown. (B) Fold increase in DN Tregs cells after 21 days of ex vivo expansion (n=8). (C) Purity of DN Tregs was assessed by flow cytometry on day 0 and day 21. Representative figure is shown.

FIG. 2 shows that DN Tregs suppress proliferation of autologous CD4$^+$, CD8$^+$ and CD19$^+$ cells. Purified naïve CD4+, CD8+ or CD19+ cells were labeled with CFSE and co-cultured with αCD3/CD28 beads or F(ab')2 fragment of goat anti-human IgM, respectively, in the presence of ex vivo-expanded DN Tregs for 4 days. Proliferation was measured by CFSE dilution. The data are expressed as mean percentage inhibition of three replicates. Error bars represent SD. The experiment was done in triplicates, and repeated 8 times (A,B) or 5 times (C) with cells obtained from different donors. Similar results were observed.

FIG. 3 shows that DN Tregs suppress secretion of IFN-γ by CD4$^+$ and CD8$^+$ T cells and IL-10 by CD4+ T cells. The concentration of IFN-γ (A) and IL-10 (B) was measured in the supernatants obtained from a 4-day suppression assay of DN Tregs and CD4$^+$ or CD8$^+$ T cells co-cultures, at 4:1, supressor-to-responder ratio. The values represent mean±SD of 3 replicates. Similar results were obtained from 3 different suppression assays, each executed with a different donor. *p<0.05, p<0.01, *p<0.001, n.d. non-detected.

FIG. 5 shows that DN Tregs delay onset of xenogeneic GVHD. 6 week old NSG mice were sublethally irradiated (250 cGy) and i.v. injected with PBMCs (n=23) obtained from a healthy human donor or DN Tregs (n=14) ex vivo-expanded from the same donor. Treated mice were infused with PBMCs followed by three injections of DN Tregs on day 0, 3 and 7 (n=14). Mice injected with PBS alone (n=12) were used as controls. Mice were monitored daily for the signs of GVHD. (B) Survival curves of recipient mice. Statistical differences between the curves were compared using log-rank test: PBMC vs Treated 3 inj., p<0.001; PBMC vs DN Treg, p<0.001; PBMC vs PBS, p<0.001. (C) Weight of mice was monitored daily to assess severity of GVHD. Mice that lost >20% of their initial body weight were euthanized. Kruskal-Wallis test was used to determine statistical significance. Survival and weight monitoring data were pooled from three separate experiments.

FIG. 6 shows that ex vivo-expanded DN Tregs can kill human cancer cells. Cytotoxicity against human leukemic (A) or lung cancer (B) cell lines by ex vivo-expanded human DN Tregs was determined by flow cytometry killing assay. In short, cancer cells were labeled with PKH and co-cultured for 2 h (A) or 16 h (B) with DN Tregs at the indicated ratios. Specific killing of cancer cells was determined by the proportion of cells remaining alive after co-incubation with DN Tregs. Similar results were obtained from 3 different donors.

FIG. 7 shows tracking and in vivo proliferation of expanded DN Tregs in NSG mice. Ex vivo-expanded DN Tregs were stained with CFSE and injected into sublethally irradiated (250 cGy) NSG mice. On days 1, 3, 5, 7 and 10, 2 to 3 mice per group were sacrificed and the following tissues were harvested: blood, bone marrow, spleen, lymph nodes, kidneys, liver and lungs. (A) The frequency of DN Tregs from each tissue was assessed by flow cytometry. (B) Analysis of proliferation of DN Tregs was assessed by CFSE dilution. Here is an example of DN Tregs isolated from the spleen.

FIG. 8 shows a) Purified naïve CD8$^+$ (right) cells (1×10$^5$/well) were labeled with CFSE and co-cultured with anti-CD3/CD28 beads in the absence or presence of ex vivo expanded allogeneic DNT (8×10$^5$/well, bottom panels) for 3 days. Proliferation of CD8$^+$ T cells was measured by CFSE dilution. Representative histograms are shown. Numbers represent the frequency of proliferating cells. Filled histograms are the CD4$^+$ or CD8$^+$ T cells cultured in media only. The experiment was performed in triplicates. b) Sublethally irradiated NSG mice were intravenously injected with 1×10$^7$ human PBMCs, DNTs or PBS (n=5 per group). On days 2, 6, 10, and 14 after injection, mouse body weight was measured. The graph shown is representative of results from five DNT and five PBMC donors. d) NSG mice injected with 5×10$^6$ human PBMC were infused with PBS (●) or 2×10$^7$ allogeneic DNTs on days 0, 3, and 6 after PBMC injection.

FIG. 9 shows that DNT cells do not kill or interfere with normal hematopoetic cells. a) Freshly isolated healthy BM cells were cultured either alone or with ex vivo expanded autologous DNT cells at a 4:1 ratio. After 12 and 24 hours of culture, cells were stained with anti-human CD34, CD3, CD33 antibodies and viability dyes, AnnexinV and eF450. The viability of CD34+CD3− (left) and CD33+CD3− (right) cells were determined using flow cytometry. (b-c) Cytotoxicity of allogeneic DNTs expanded from three HDs against CD34− AML, OCI/AML3, primary AML patient blasts, 110164 and 090596, and normal PBMCs from two HDs (b) or against CD34+ AMLs, 130723, 090240, and 130624 and HSPCs from two different HDs (c) at 4-to1 effector-to-target ratios was determined using the 2-hour flow-based killing assay. d) Freshly harvested BM cells were injected directly into the left femurs of NSG mice (5×106/mouse, n=8). 1 day later, half of the mice were injected i.v. with ex vivo expanded autologous DNTs (5×106/mouse), and half (n=4) were injected with PBS as controls. BM from each mouse was harvested 5 days later, stained with anti-human CD34 antibody and the cell viability dyes Annexin V and eF450, and analyzed by flow cytometry. Bar graph shows the total number of human CD34+ cells in mouse BM in both groups. Error bars represent mean±SD. (e and f) CD133+CD34+ human HSPCs were intravenously injected into sublethally irradiated NSG mice (3×105 cells/mouse, n=13). Eight weeks post HSPC injection, 7 of the 13 mice were intravenously injected with 107 ex vivo expanded allogeneic DNTs and the rest were injected with PBS. To determine chimerism originating from the HSPC population, cells from BM, spleen, and PB were harvested 8 weeks after DNT injection and were stained with anti-mouse CD45, anti-human CD45, CD3, CD19, CD11b, CD56, CD33, and CD34 antibodies. The percentage of human leukocytes e) and its subsets f) were determined by flow cytometry analysis. Horizontal bars represent the mean value and the error bars represent SEM of each group.

DETAILED DESCRIPTION

Figures 1A, 1B, 1C:
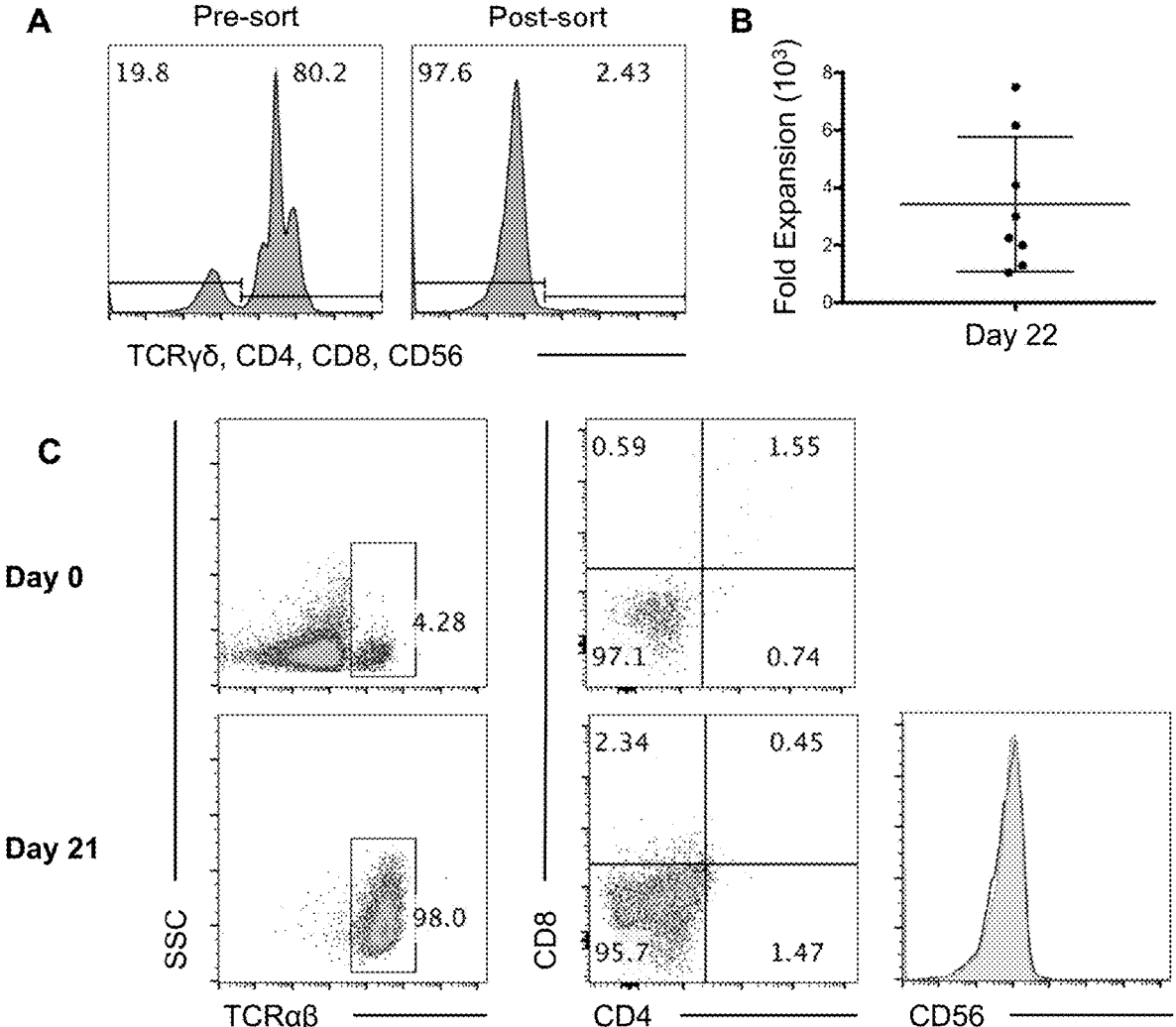
FIGS. 1A-1C.

In order to accelerate the clinical use of human DN Tregs, the present method was developed that allows for a large-scale (~4000 fold) ex vivo expansion of human DN Tregs and it was demonstrated that ex vivo-expanded human DN Tregs can suppress CD4$^+$ and CD8$^+$ T cell, and CD19$^+$ B cell proliferation and kill various cancer cell lines in vitro. Human DN Tregs does not induce xenogeneic GVHD after infusion into immunodeficient mice and can delay an onset of xenogeneic GVHD induced by human PBMC. There is therefore provided herein a method for large scale ex vivo expansion of dual functional human αβ-TCR$^+$CD4$^-$CD8$^-$CD56$^-$ regulatory T cells.

In an aspect, there is provided a method for expanding human CD4$^-$CD8$^-$ regulatory T cells (DN Tregs) from a population of cells comprising DN Tregs, comprising: culturing the population of cells with antigen presenting cells (APCs), preferably the DN Tregs are αβ-TCR$^+$CD56$^-$, γδ-TCR+, or both.

The term "double negative Treg cell" may mean a T lymphocyte that expresses CD3 but lacks the cell surface expression of CD4 and CD8. The DN T cells will express a T-cell receptor (TCR) which can be either the αβ or the γδ TCR.

An antigen presenting cell (APC) or accessory cell is a cell that displays typically foreign antigens complexed with major histocompatibility complexes (MHCs) on their surfaces; this process is known as antigen presentation. T-cells may recognize these complexes using their T-cell receptors (TCRs). These cells process antigens and present them to T-cells. Artificial antigen presenting cells are synthetic versions of APCs and are made by attaching the specific T-cell stimulating signals to various macro and micro biocompatible surfaces. Cell-based artificial antigen presenting cells are also known in the art. Cell based aAPCs can be made, for example, by transfecting cells to express specific antigens, and optionally co-stimulatory or cells adhesion molecules. A person skilled in the art would understand the scope and types of APCs (and associated co-stimulatory or cells adhesion molecules) that could be used in the present methods, based on the present disclosure.

In an embodiment, the APCs are artificial APCs displaying anti-CD3 antibodies and at least one cell surface adhesion molecule for immunological synapse. Optionally, the cell surface adhesion molecule is at least one of CD54 and CD58.

In some embodiments, the APCs further express a co-stimulatory molecule, preferably at least one of CD80, CD86, CD83, 4-1BBL, OX40L, ICOSL, CD40L, and CD28 antibody.

In some embodiments, the APCs do not express inhibitory molecules, such as PDL1, PDL2, B7H3 and B7H4.

In some embodiments, the APCs further express at least one of M-CSF, IL-6, IL-8, TGF-β and MIP-1a.

In some embodiments, the APCs further express IL-7, IL-15 and/or IL-2.

In some embodiments, the APCs comprise K562-based artificial APCs, preferably as set forth in Tables 1 and 2.

TABLE 1

| K562-based artificial APCs for natural killer cell and Treg clinical studies | | | | | |
|---|---|---|---|---|---|
| K562-based aAPC and transduced molecules | Target disease | Target cell for expansion and notes | Phase | Status | Ref. |
| K562-mbIL15-41BBL: 4-1BBL, membrane-bound IL-15 | Relapsed high risk multiple myeloma | Autologous NK cell plus bortezomib | I | Open | NCT01212897; University of Arkansas |
| | Asymptomatic multiple myeloma post standard therapy | Autologous NK cells | I | Open | NCT01884688; University of Arkansas |
| aAPC (clone #9): CD64, CD86, 4-1BBL, truncated CD19, membrane bound IL-21 | B-cell chronic lymphocytic leukemia undergoing umbilical cord SCT | Allogeneic NK cells derived from cord blood | I | Open | NCT01619761; DACC |
| | Multiple myeloma undergoing umbilical cord SCT | Allogeneic NK cells derived from cord blood | I | Open | NCT01729091; |
| | Myeloid leukemia undergoing SCT | Allogeneic NK cells derived from cord blood | I | Open | MDACC NCT01823198; MDACC |
| KT64/86: CD64, CD86 | Advanced hematologic malignancies with umbilical cord SCT | Natural Treg from umbilical cord cells expanded with aAPC loaded with OKT3 | I | Open | NCT00602693; University of Minnesota | aAPC, artificial antigen presenting cell;

CAR, chimeric antigen receptor;

DFCI, Dana-Farber Cancer Institute;

GFP, green fluorescence protein;

EBV, Epstein-Barr virus;

mIL-15, membrane bound IL-15;

mIL-21, membrane bound IL-21;

MDACC, M.D. Anderson Cancer Center;

MTD, maximum tolerated dose;

NCI, National Cancer Institute;

PMCC, Princess Margaret Cancer Centre;

SCT, stem cell transplant

TABLE 2

K562-based artificial APCs for anti-tumor T-cell clinical studies

| K562-based aAPC and transduced molecules | Target disease | Target cell for expansion and notes | Phase | Status | ClinicalTrials.gov Identifier |
|---|---|---|---|---|---|
| aAPC-A2, clone 33: HLA class I, CD80, CD83 | Advanced melanoma | Autologous aAPC-generated MARTI T cells | I | Closed | NCT00512889; DFCI; future studies at Princess Margaret |
| 7F11ECCE: CD64, 4-1BBL | Advanced melanoma | TIL for transfer after lymphodepletion using aAPC loaded with OKT3 | II | Closed | NCT01369875; NCI |
| K562cs: CD32, CD80, CD83, CD86, 4-1BBL | EBV-positive lymphoma | EBV-specific T cell lines, aAPC used for costimulation, not antigen-specific stimulation | I | Open | NCT01555892; Texas Children's and Methodist Hospital |
| aAPC (clone #4): CD64, CD86, 4-1BBL, truncated CD19, membrane-bound IL-15 | B-Lineage Lymphoid Malignancies After Auto-SCT | Autologous CD19-specific CAR T cells | I | Open | NCT00968760; MDACC |
| | B-Lineage Lymphoid Malignancies after Umbilical Cord SCT | Allogeneic CD19-specific CAR T cells derived from cord blood | I | Open | NCT01497184; MDACC |
| | | Allogeneic CD19-specific CAR T cells | I | Open | NCT01362452; MDACC |
| | B-Lineage Lymphoid Malignancies after allo-SCT B-cell Chronic Lymphocytic Leukemia | Autologous CD19-specific CAR T cells | I | Open | NCT01653717; MDACC |

In alternate embodiments, the APCs are autologous APCs, preferably, dendritic cells, monocytes or activated B cells.

In some embodiments, the culturing is additionally in the presence of IL-2.

In some embodiments, the culturing is additionally in the presence of IL-7 and/or IL-15.

In some embodiments, the method further comprises activating the population with anti-CD3 antibodies prior to culturing with the APCs. Optionally, the activating is with anti-CD3 antibodies cross-linked, or otherwise attached, to a surface or alternatively, with soluble anti-CD3 antibodies.

In some embodiments, the activating is sequentially with anti-CD3 antibodies cross-linked, or otherwise attached, to a surface and soluble anti-CD3 antibodies.

In some embodiments, the method further comprises at least partially depleting the population of non-DN Tregs cells prior to culturing and/or activating. Optionally, the population is depleted based on a cell surface marker, preferably using antibodies to the cell surface marker bound to magnetic beads. The cell surface marker is preferably at least one of CD4$^+$, CD8$^+$, CD56$^+$ and γδ-TCR$^+$. Following culturing the population may be further depleted this manner.

In some embodiments, the population comprises peripheral blood mononuclear cells (PBMCs) or cord blood mononuclear cells (CBMCs).

In some embodiments, the method further comprises incubating the expanded DN Tregs with at least one inhibitor of the PI3K/AKT/mTOR pathway.

Four classes of inhibitors that will inhibit the PI3K/AKT/mTOR pathway are currently identified. Many such inhibitors are known in the art and currently in clinical trials. In some embodiments, those upstream of the signaling cascade are used with the method described herein. A review by Dienstmann et al.[30] includes inhibitors that are currently in clinical trials for cancer treatment.

In some embodiments, the inhibitor is a mTOR inhibitor, dual PI3K/mTOR inhibitor, AKT inhibitor, or Pan-class I and isoform-specific PI3K inhibitors. Preferably, the inhibitor is a Rapalog, further preferably, rapamycin, deforolimus, emsirolimus, everolimus, ridaforolimus, temsirolimus or a mTORC1/mTORC2 dual inhibitor.

In other embodiments, the inhibitor is Wortmannin, LY294002, PKI-179, or Akt inhibitor IV.

In an aspect, there is provided a population of DN Tregs obtained by the methods described herein.

In an aspect, there is provided a use of DN Tregs for the treatment of cancer, preferably leukemia or lung cancer.

In an aspect, there is provided a use of DN Tregs in the preparation of a medicament for the treatment of cancer, preferably leukemia or lung cancer.

In an aspect, there is provided a method of treating cancer in a subject, preferably leukemia or lung cancer, comprising administering to the subject a therapeutically effective amount of DN Tregs.

In an aspect, there is provided a use of DN Tregs for the treatment or prevention of allograft rejection, GVHD, or an autoimmune disease. Given the examples provided herein, it is anticipated that DN Tregs could be used to treat or prevent allograft rejection, GVHD, or an autoimmune disease, preferably graft rejection, in humans. In some embodiments, the DN Tregs are αβ-TCR$^+$. In other embodiments, the DN Tregs are Δδ-TCR$^+$.

In an aspect, there is provided a use of DN Tregs in the preparation of a medicament for the treatment or prevention of allograft rejection, GVHD, or autoimmune diseases.

In an aspect, there is provided a method of treating or preventing allograft rejection, GVHD, or an autoimmune disease, comprising administering to the subject a therapeutically effective amount of DN Tregs.

The term "effective amount" as used herein means an amount effective, at dosages and for periods of time necessary to achieve the desired result, e.g. to treat a tumor.

The term "treating" includes, but is not limited to, alleviation or amelioration of one or more symptoms or conditions of a disease or condition (such as cancer, autoimmune disease, allergy, infection etc.), diminishment of extent of disease, stabilized state of disease, preventing spread of disease, delaying or slowing of disease progression, and amelioration or palliation of the disease state, remission whether detectable or undetectable and/or prolonged survival as compared to expected survival if not receiving treatment.

The compositions described herein can be prepared by per se known methods for the preparation of pharmaceutically acceptable compositions which can be administered to subjects, such that an effective quantity of the cells is combined in a mixture with a pharmaceutically acceptable vehicle. Suitable vehicles are described, for example, in Remington's Pharmaceutical Sciences (Remington's Pharmaceutical Sciences, 20th ed., Mack Publishing Company, Easton, Pa., USA 2000). On this basis, the compositions include, albeit not exclusively, solutions of the substances in association with one or more pharmaceutically acceptable vehicles or diluents, and contained in buffered solutions with a suitable pH and iso-osmotic with the physiological fluids.

An effective amount of the composition may vary according to factors such as the disease state, age, sex, and weight of the individual, and the ability of the cells to elicit a desired response in the individual. Dosage regime may be adjusted to provide the optimum therapeutic response. For example, several divided doses may be administered daily or the dose may be proportionally reduced as indicated by the exigencies of the therapeutic situation.

The pharmaceutical compositions of the invention may include other active agents that are useful in treating the disease or condition to be treated. For example, in the treatment of a tumor, other anti-cancer agents may be administered either in the same composition or in a separate composition.

The advantages of the present invention are further illustrated by the following examples. The examples and their particular details set forth herein are presented for illustration only and should not be construed as a limitation on the claims of the present invention.

Examples

Methods
Ex Vivo Expansion of DN Tregs

DN Tregs comprise about 1% of peripheral T cells of healthy adults. To expand human DN Tregs, PBMCs were isolated by Ficoll density gradient and DN Treg population was enriched by depleting population of T cells and NK cells that would be prone to outgrow using this expansion method. In short, PBMCs were stained with FITC conjugated antibodies to CD4, CD8, CD56 and TCRγδ markers, and anti-FITC magnetic beads (Miltenyi Biotec) (FIG. 1A). From 50-80 ml of blood, we were able to obtain $5\text{-}25\times10^5$ DN Tregs. After sorting, cells were resuspended in RPMI media supplemented with 10% FBS and recombinant human (rh)IL-2. In order to activate DN Tregs, cells were seeded in the tissue culture plate coated with CD3 monoclonal antibody (OKT3). On day 3 of culture, cells were harvested, washed and cultured for another 4-7 days in the presence of rhIL-2 and rhIL-7 and/or rhIL15 followed by co-culture with lethally irradiated (150 Gy) aAPCs in the presence of rhIL-2 and rhIL-7 and/or rhIL15. DN Tregs were used for functional assays on day 22. The phenotype of the cells was assessed regularly to monitor for potential outgrowth of $CD4^+$, $CD8^+$, $CD56^+$ or TCRγδ cells. If other cells besides DN Tregs were present, they were depleted using magnetic beads sorting. By day 22, the average purity of DN Tregs was 95.48±2.49% (FIG. 1C). We were able to obtain 1-18× $10^8$ cells, with the average fold expansion of 3900±2835 (FIG. 1B).

Results and Discussion

Ex Vivo Expanded DN Tregs are Potent Suppressors In Vitro

Figures 2A, 2B, 2C:
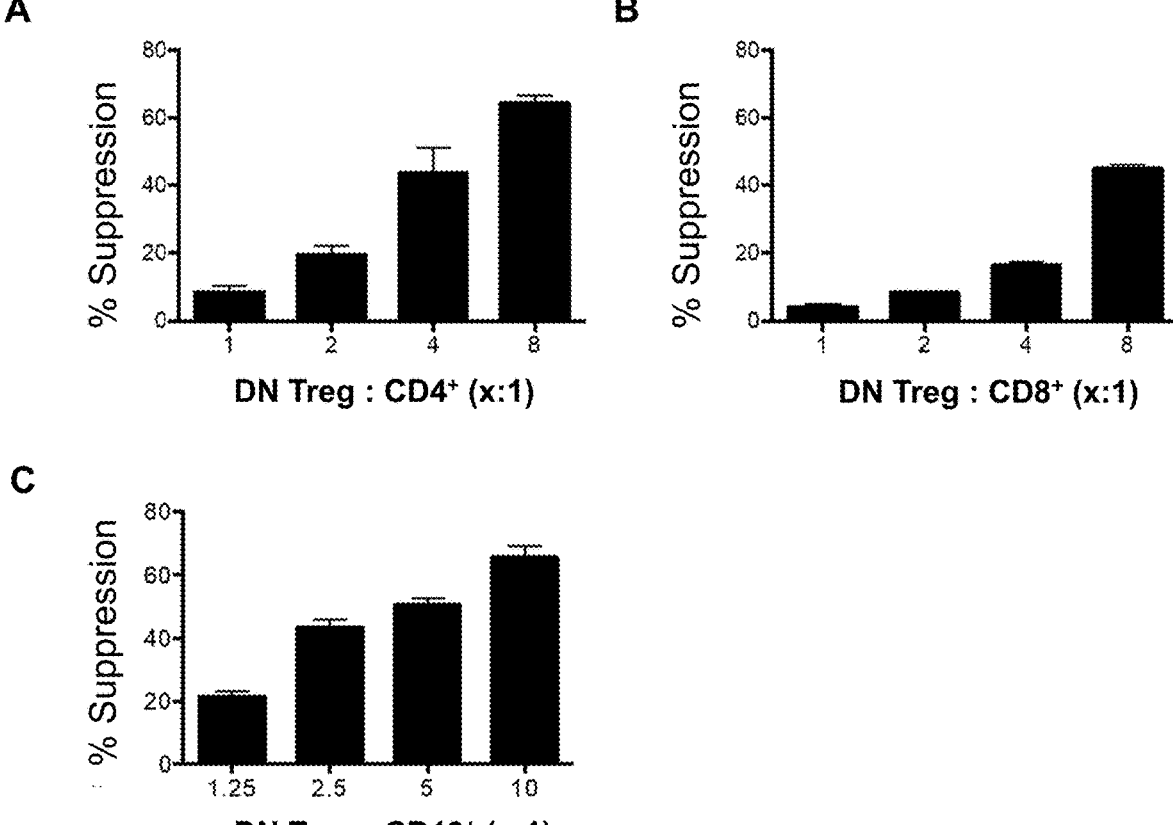
FIGS. 2A-2C.
Figures 3A, 3B:
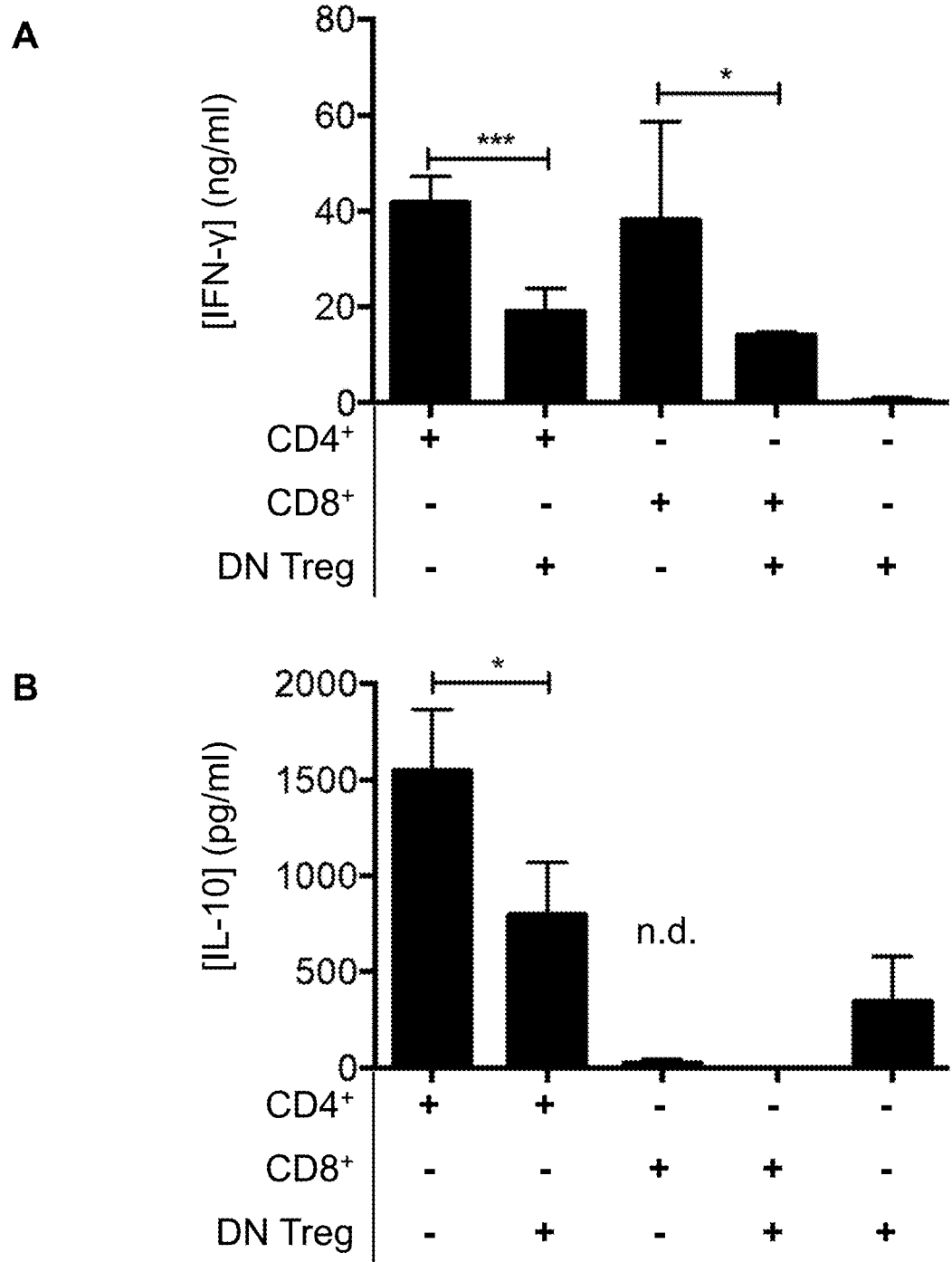
FIGS. 3A-3B.

Previously, human DN Tregs that were activated by allogeneic DCs have been shown to suppress proliferation of $CD4^+$ T cells in antigen- and allo-specific manner[31-34] However, whether poly-clonally activated and ex vivo-expanded DN Tregs can retain their suppressive function has not been studied previously. Thus, we evaluated the ability of ex vivo-expanded DN Tregs to inhibit proliferation of autologous $CD4^+$ and $CD8^+$ T cells, as well as $CD19^+$ B cells. To this end, CFSE-labeled T cells or B cells were stimulated with αCD3/CD28 coated beads, or F(ab')2 fragment of IgM, respectively, and co-cultured in the presence or absence of DN Tregs at increasing ratios. After 4-5 days of co-culture, proliferation of responder cells was assessed by CFSE-dilution using flow cytometry. DN Tregs were found to potently suppress proliferation of $CD4^+$ T cells (FIG. 2A), $CD8^+$ T cells (FIG. 2B) and $CD19^+$ B cells (FIG. 2C) in a dose-dependent manner. Interestingly, suppression of $CD4^+$ T cells by DN Tregs was consistently stronger than suppression of $CD8^+$ T cells for all the donors that we have tested. Furthermore, $CD4^+$ T cells produce IL-10 (FIG. 3B) and both $CD4^+$ and $CD8^+$ T cells produced high amounts of IFN-γ upon stimulation with αCD3/CD28 beads (FIG. 3A). However, upon addition of DN Tregs to cell cultures at 4:1, suppressor-to-responder ratio, the amount of IFN-γ and IL-10 released by the responder cells was significantly reduced, thus suggesting DN Treg-mediates suppression of activation of responder cells.

Rapamycin Augmented Immunosuppressive Function of DN Tregs

Figure 4:
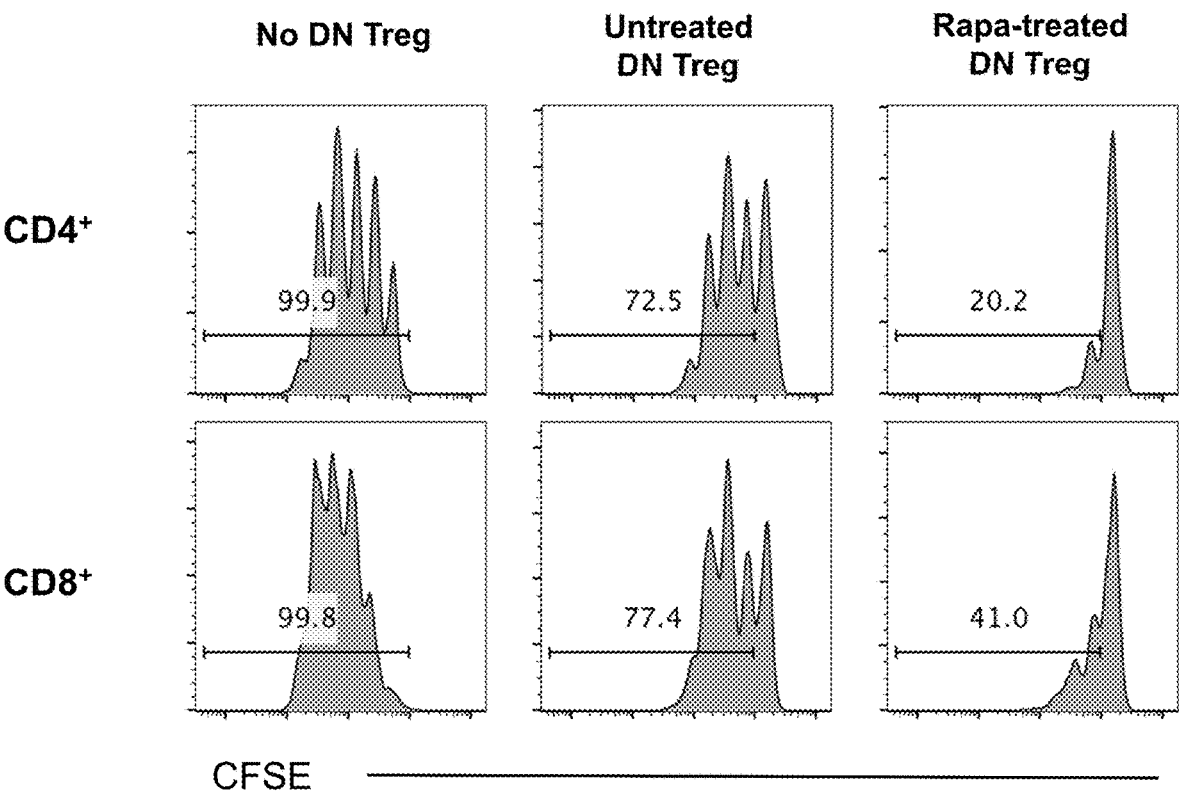
FIG. 4 shows that Rapamycin-treated DN Tregs manifest augmented regulatory function. Ex vivo-expanded DN Tregs were pre-incubated with Rapamycin for 2 h, washed extensively and used as suppressor cells in a suppression assay against autologous CD4$^+$ and CD8$^+$ T cells stimulated with αCD3/CD28 beads. On day 3, proliferation of responder cells was quantified by CFSE dilution. The histograms represent proliferation of responder cells at 1:1, supressor-to-responder cells ratio. The number represent percentage of proliferating responder cells. Similar results were observed in 3 independent experiments.

Rapamycin is an mTOR inhibitor and has been shown to facilitate nTreg expansion and regulatory function[35]. Therefore, we investigated whether the inhibition of Akt/mTOR pathway by Rapamycin could improve immunosuppressive function of DN Tregs. For this purpose, ex vivo-expanded DN Tregs were pre-incubated with Rapamycin for 2 hours, extensively washed and used in the suppression assay. Blockade of the Akt/mTOR pathway by Rapamycin rendered DN Tregs more immunosuppressive as they inhibited proliferation of autologous $CD4^+$ and $CD8^+$ T cells to a greater extent than non-treated DN Treg, as assessed by CFSE dilution (FIG. 4). Suppression of $CD4^+$ T cells increased significantly by almost 52±2% at the suppressor-to-responder ratio of 1:1. Since DN Tregs always exerted more modest suppression against $CD8^+$ cells, Rapamycin-treated DN Tregs demonstrated significant improvement in their suppressive activity by 37±1% at 1:1, suppressor-to-responder ratio.

Ex Vivo Expanded DN Tregs Delayed Onset of Xenogeneic GVHD in NSG Mice

Figure 5A:
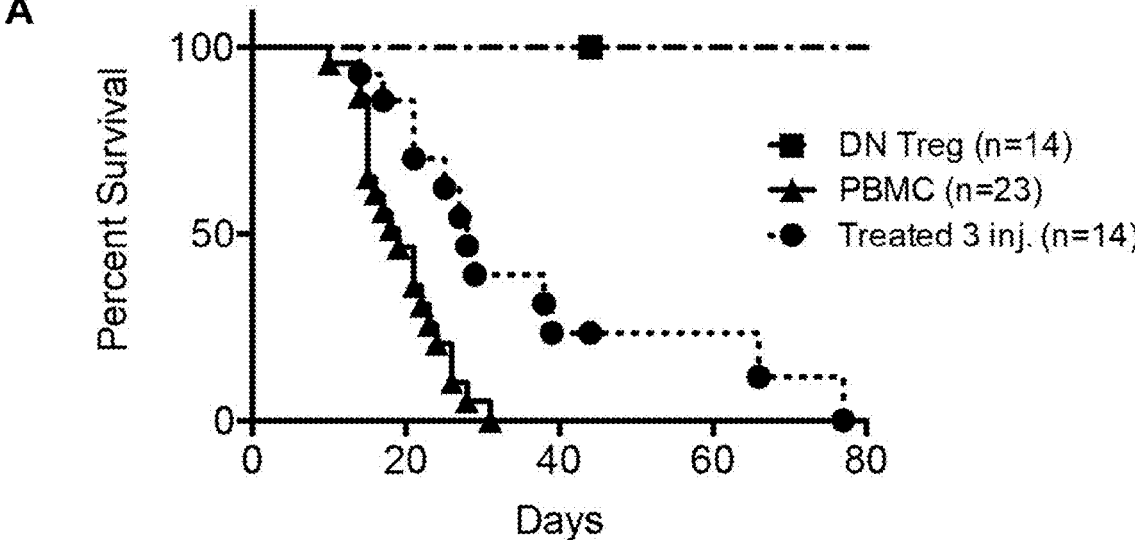
FIGS. 5A-5B.
Figure 5B:
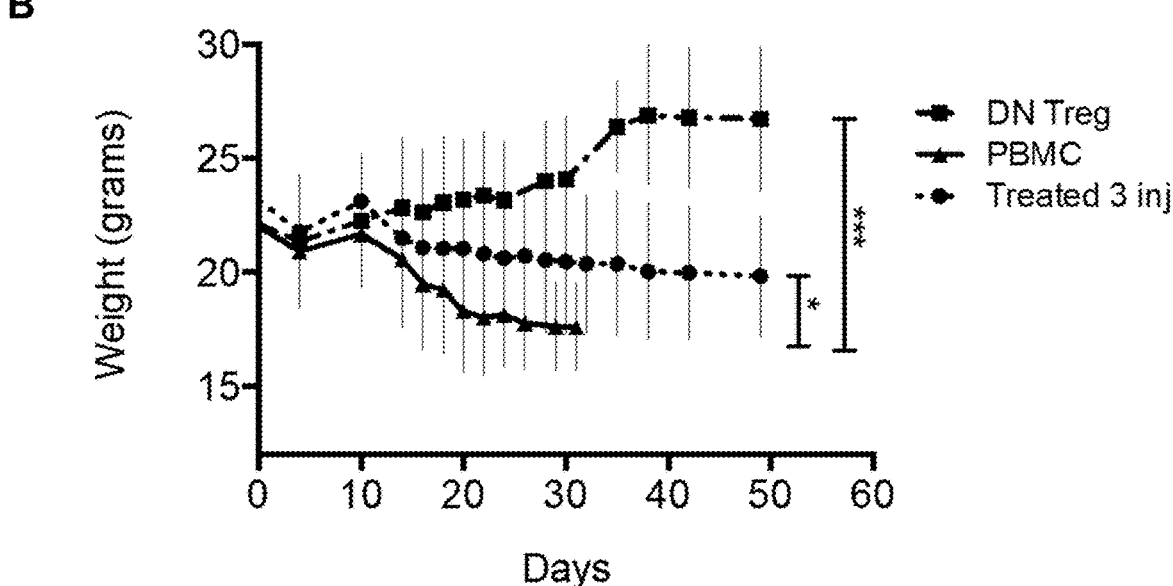
Figure 7A:
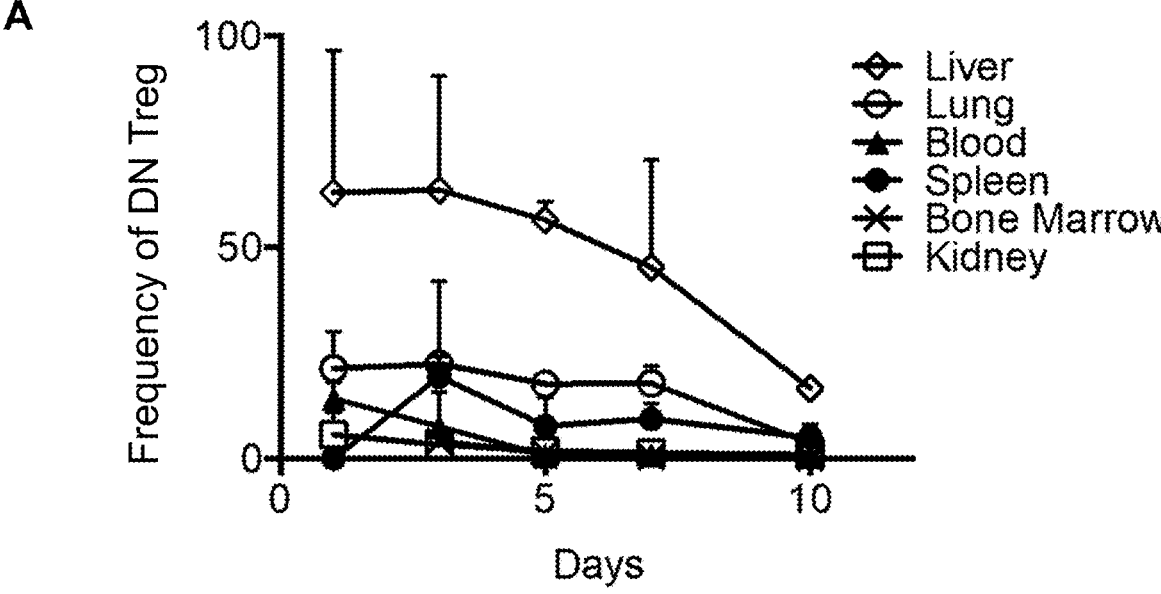
FIGS. 7A-7B.
Figure 7B:
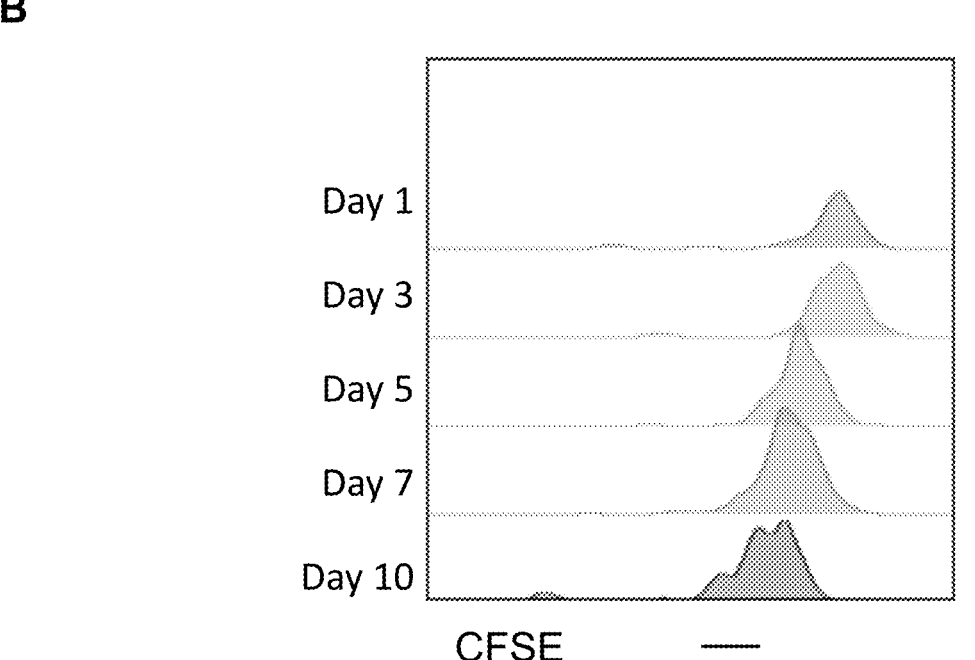

For evaluation of the in vivo effects of ex vivo expanded human DN Tregs, PBMCs were freshly isolated from peripheral blood of the same donor and infused into sublethally irradiated NSG mice to induce xenogeneic GVHD. To ameliorate GVHD, we proposed treatment regimen that involved injection of 3 doses of DN Tregs over the span of first week since induction of GVHD. Mice receiving PBMC injection developed GVHD and all animals were dead by 31 days with the mean survival time (MST) of 19 days (FIG. 5A). In most cases, death was attributable to sever weight loss (FIG. 5B). Recipients of adoptive transfer of 3 doses of DN Tregs significantly delayed onset of GVHD (MST=29, p<0.001), with the last subject surviving for 77 days. Importantly, mice injected solely with DN Tregs remain healthy, as all mice remained alive 100 days post injection without development of clinical signs of GVHD (FIG. 5B), thus highlighting the safety and lack of immunogenicity of DN Tregs. Furthermore, in vivo DN Tregs traffic to many hematopoietic and lymphoid tissues, including peripheral blood, bone marrow, spleen and lymph nodes, as well as other organs including lung, liver and kidneys (FIG. 7A). DN Tregs proliferate in vivo and can be found in the tissues 10 days post injection (FIG. 7B).

Ex Vivo Expanded DN Tregs can Kill Human Cancer Cells

Figure 6A:
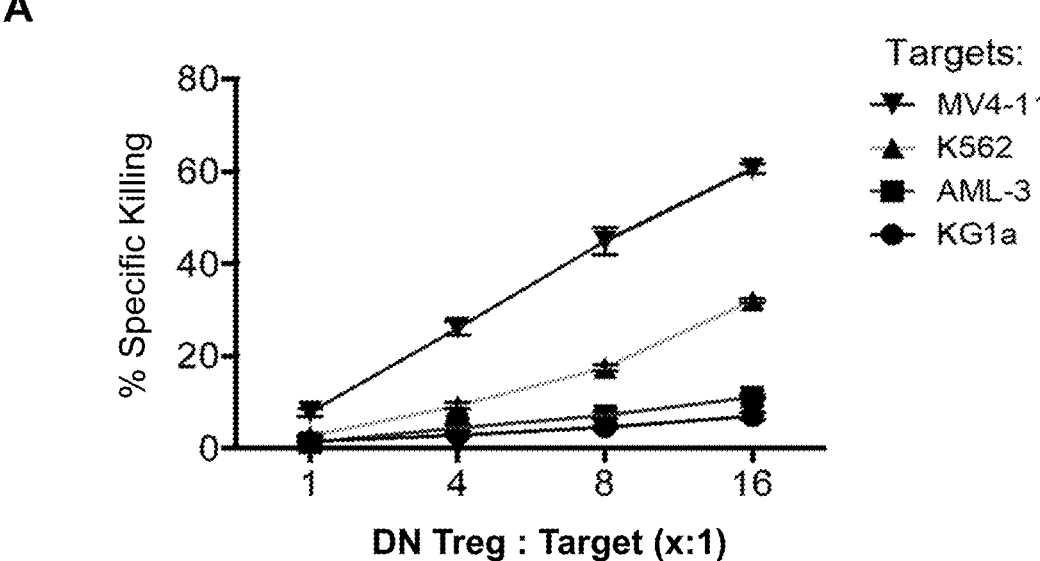
FIGS. 6A-6B.
Figure 6B:
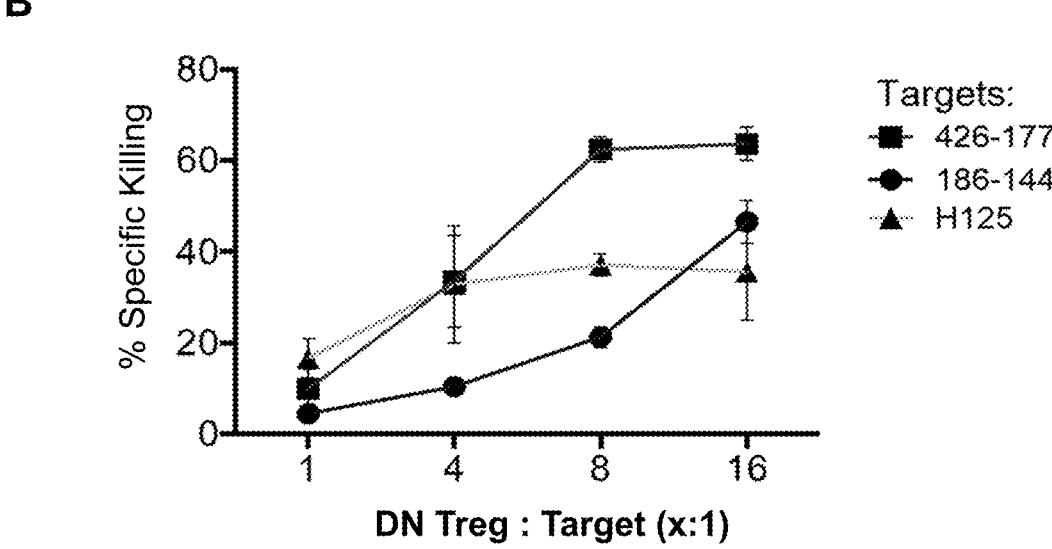

Previously, we demonstrated that both mouse TCRαβ[+] and TCRγδ[+] populations sorted from DN T cells expanded from peripheral blood of AML patients in complete remission were cytotoxic against autologous and allogeneic leukemic blasts in vitro[6]. Therefore, we wanted to test whether DN Tregs expanded by the means of a novel protocol also demonstrate cytotoxic function against various human cancer cell lines. To assess DN Treg-induced killing of cancer, a flow cytometry-based killing assay was adapted in which target cells were stained with PKH-26 before co-culture with DN Tregs. The percentage of cytotoxicity in the PKH-26-gated cell population was calculated as described in methods. DN Tregs exerted dose-dependent cytotoxicity against all human primary lung cancer cell lines that were tested: 186-144, 426-177 and H125 lines (FIG. 6B). It was also found that DN Tregs effectively killed leukemic MV4-11 and K562 cells lines, but were less cytotoxic toward AML-3 and KG1a cells lines (FIG. 6A). These findings demonstrate that DN Tregs not only exhibit immunoregulatory function, but also are cytotoxic to cancer.

The protocol described above allows for large-scale ex vivo expansion of human DN Tregs. DN Tregs are co-cultured with irradiated artificial APC (human K562 cell line with surface expression of a transduced membranous form of anti-CD3 mAb, CD80, CD83, and 4-1BBL)[29], in the presence of combination of cytokines. Using this protocol, up to ~10[9] huDN Tregs (~4000-fold expansion) from 50-80 ml blood were obtained in 3 weeks (FIG. 1B) with very high purity (FIG. 1C). Importantly, these ex vivo-expanded DN Tregs can suppress in vitro the proliferation of both CD4[+] and CD8[+] T cells (FIG. 2A-B), as well as CD19[+] B cells (FIG. 2C) stimulated in a polyclonal manner. Moreover, DN Tregs were found to kill various leukemic and lung cancer cell lines. While infusion of human peripheral blood mononuclear cells (PBMC) into immunodeficient NSG mice induces severe acute xenogeneic GVHD, infusion of ex vivo expanded human DN Tregs did not cause GVHD or tissue damage in recipients. Furthermore, treatment with DN Tregs significantly delayed an onset of xenogeneic GVHD in humanized mouse model. The ability to obtain large numbers of functional DN Tregs not only makes it possible, for the first time, to study their function and mechanisms of action in vivo, but also indicates the possibility of using ex vivo-expanded human DN Tregs to treat various diseases such as allograft rejection, GVHD, autoimmune diseases and malignant diseases.

Graft-vs-Leukemia (GVL) and Graft-vs-Host Disease (GVHD)

Hematopoietic stem cell transplantation from a matched related or unrelated donor is considered standard of care in eligible patients with high risk clinical, cytogenetic and molecular features.(S1, S2) This is also the only potentially curative treatment for AML patients with relapsed disease. (S3-S7) ENREF 7. The role of HSCT in patients with positive MRD status is also increasingly important.(S8) The efficacy of HSCT in AML is based on the intensity of the conditioning regimen as well as the immune mediated anti-tumour activity of the graft-vs-leukemia (GVL) effect. (S9) This effect was identified when it was noted that HSCT recipients who developed acute and chronic GVHD had a lower incidence of relapse.(S10) This effect is mediated through the action of cytotoxic donor T-cells and NK cells. However, donor T cells commonly recognize normal host tissue and cause detrimental, and even lethal GVHD(S11, S12), compromising the overall benefit of allo-HSCT on patient survival. The toxicity of the conditioning regimens and complications of GVHD result in significant treatment related mortality. Over time advances in antimicrobial therapy, reduction of regimen toxicity and improvements in the prevention and treatment of GVHD have considerably reduced but not eliminated non-relapse mortality.(S13) Furthermore, broad application of allo-HSCT is limited by recipient fitness and availability of suitable donors in a timely manner. Reduced intensity conditioning regimens were devised in an effort to capitalize on the GVL effect as a therapeutic measure in the absence of the toxicity associated with intense myeloablative conditioning regimens. (S14, S15) Further refinement of this concept based around the harnessing of the GVL effect to achieve effective disease control while reducing the risk of GVHD has resulted in the development of immune cell therapies.(S16-S18)

Mouse DNT Cells and their Role in GVL and GVHD

DNT cells are mature T lymphocytes that comprise ~1% of peripheral blood mononuclear cells (PBMC) in mice, rats and humans. DNT cells express CD3 and αβ- or γδ-TCR, but not CD4, CD8 or NK cell markers nor bind invariant natural killer T (iNKT) cell specific αGalCer-loaded CD1d tetramers, thus differ from conventional T cells, NK cells and NKT cells. The Zhang lab was the first to characterize DNT cells(S19) and showed in vivo that unlike conventional CD4[+] or CD8[+] T cells, infusion of mouse allogeneic DNT cells not only did not induce GVHD, but in fact inhibited GVHD induced by allogeneic CD4[+] and CD8[+] T cells(S20-S22). Other labs have demonstrated that infusion of fully allogeneic DNT cells did not cause GVHD and could facilitate HSPC engraftment in mouse models of allogeneic bone marrow transplantation studies(S23)). In addition to suppressing unwanted GVHD, DNT cells have potent anti-cancer activity. The Zhang lab demonstrated that injection of mouse DNT cells rescued the recipients from a lethal dose of lymphoma cells(S24). The mechanisms by which mouse DNT cells suppress allogeneic immune responses and kill cancer cells have been studied extensively by the Zhang lab and others.

Safety Studies of Human Allogeneic DNT Cells

Figures 8A, 8B, 8C, 8D:
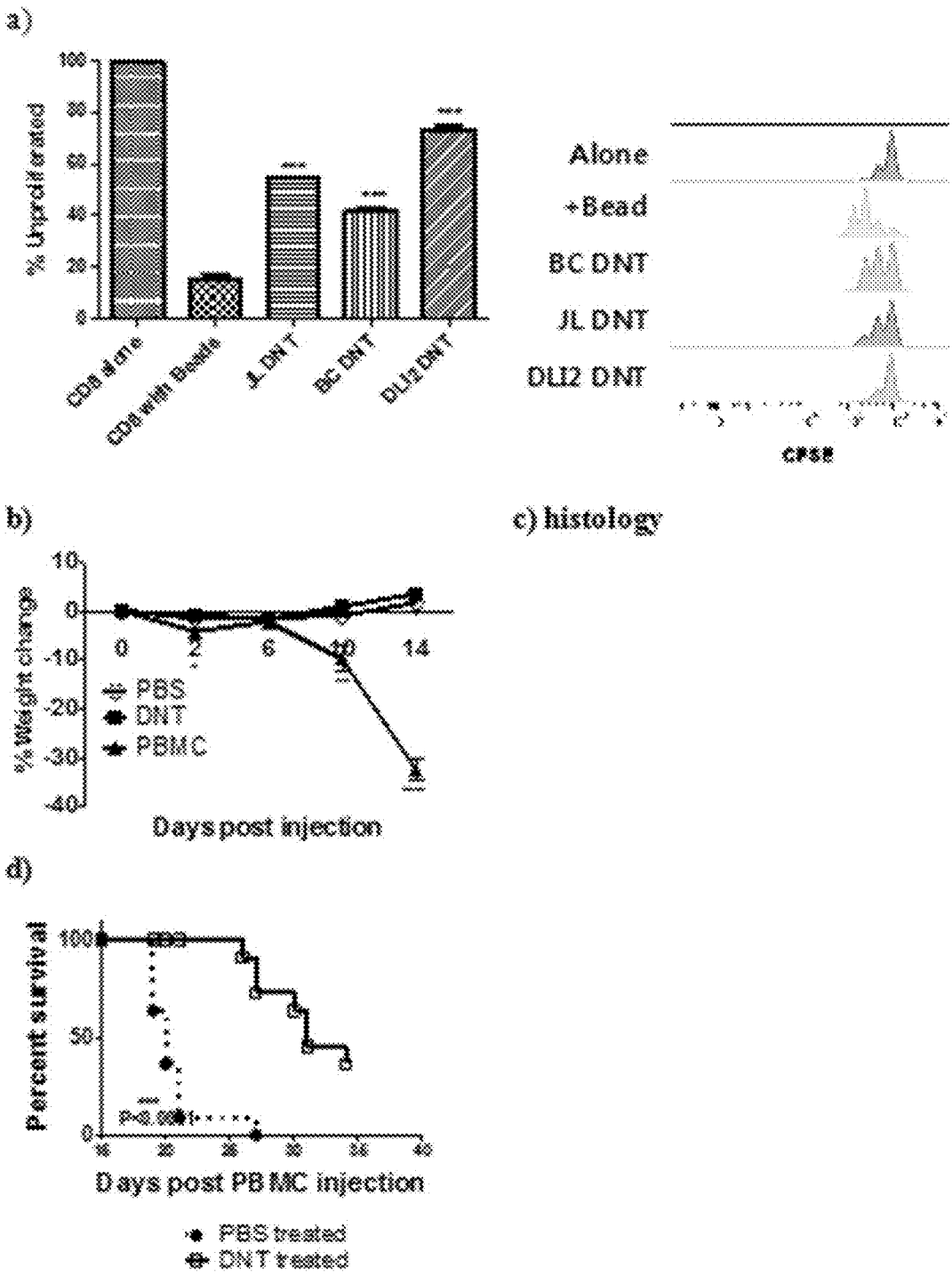
FIGS. 8A-8D.

We and others have demonstrated that injection of allogeneic mouse DNT cells does not cause GVHD and can inhibit GVHD induced by infusion of allogeneic CD4+ and CD8+ T cells (S20, S22, S23). Similar to mouse DNTs, human DNTs inhibited proliferation of CD4[+] and CD8[+] T cells in vitro (FIG. 8a). In patients who received allogeneic HSCT, a higher frequency of DNTs was associated with a reduced severity of GVHD(S25, S26), suggesting a beneficial effect of DNT cells. To validate the role of ex vivo expanded human DNT cells in the context of GVHD, we used the state-of-the-art xenograft models. All immune deficient NSG mice injected with bulk human PBMC developed lethal xeno-GVHD(S27-S29), while none of the mice injected with DNT cells developed GVHD, measured by body weight (FIG. 8b) and confirmed by histology of GVHD target organs such as the liver, skin, intestine and lungs (FIG. 8c). Furthermore, treatment with DNTs significantly prolonged survival of NSG mice from lethal xeno-GVHD caused by human PBMC (FIG. 8d). Collectively, these data suggest the potential of using DNTs to modulate GVHD associated with allo-HSCT.

Figures 9A, 9B, 9C, 9D:
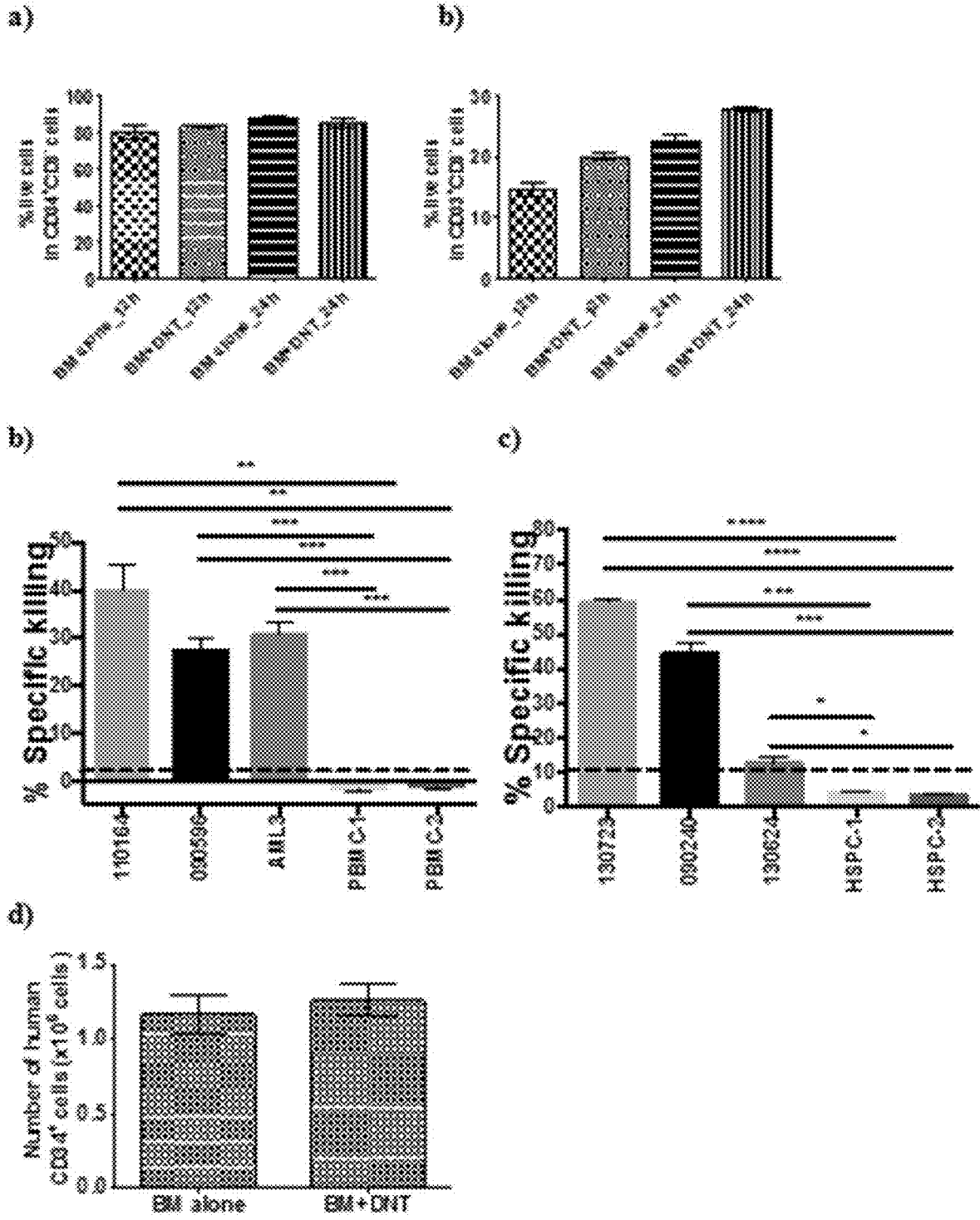
FIGS. 9A-9F.

Given that DNTs were cytotoxic to primary CD34$^+$ leukemic cells in vitro, and able to reduce leukemic engraftment in vivo8, it was critical to assess the potential cytotoxicity of DNTs against normal cells. An ideal experiment would be to test whether DNTs are cytotoxic to normal CD34$^+$ stem cells. Since there is no definitive cell surface marker for sorting normal versus leukemic CD34$^+$ cells, alternatively, healthy donor BM cells were co-cultured in vitro with ex vivo expanded DNTs. In both CD33$^+$ myeloid and CD34$^+$ HSPC enriched populations, no differences in cell viability were detected between the DNT-treated and control groups after 12 and 24 hours co-culture (FIG. 9a). Importantly, allogeneic DNT cells expanded from healthy donors are not cytotoxic to normal PBMC (FIG. 9b) or CD34$^+$CD133$^+$ human hematopoietic stem/progenitor cells (HSPC) in vitro (FIG. 9c). To further assess the effect of DNTs on normal BM cells in vivo, healthy donor BM cells were injected into NSG mice, followed by PBS or autologous DNT treatment. Five days after DNT injection, the total numbers of viable human CD34$^+$ cells were measured, and again no differences were observed between the control and treatment groups (FIG. 9d).

Figures 9E, 9F:
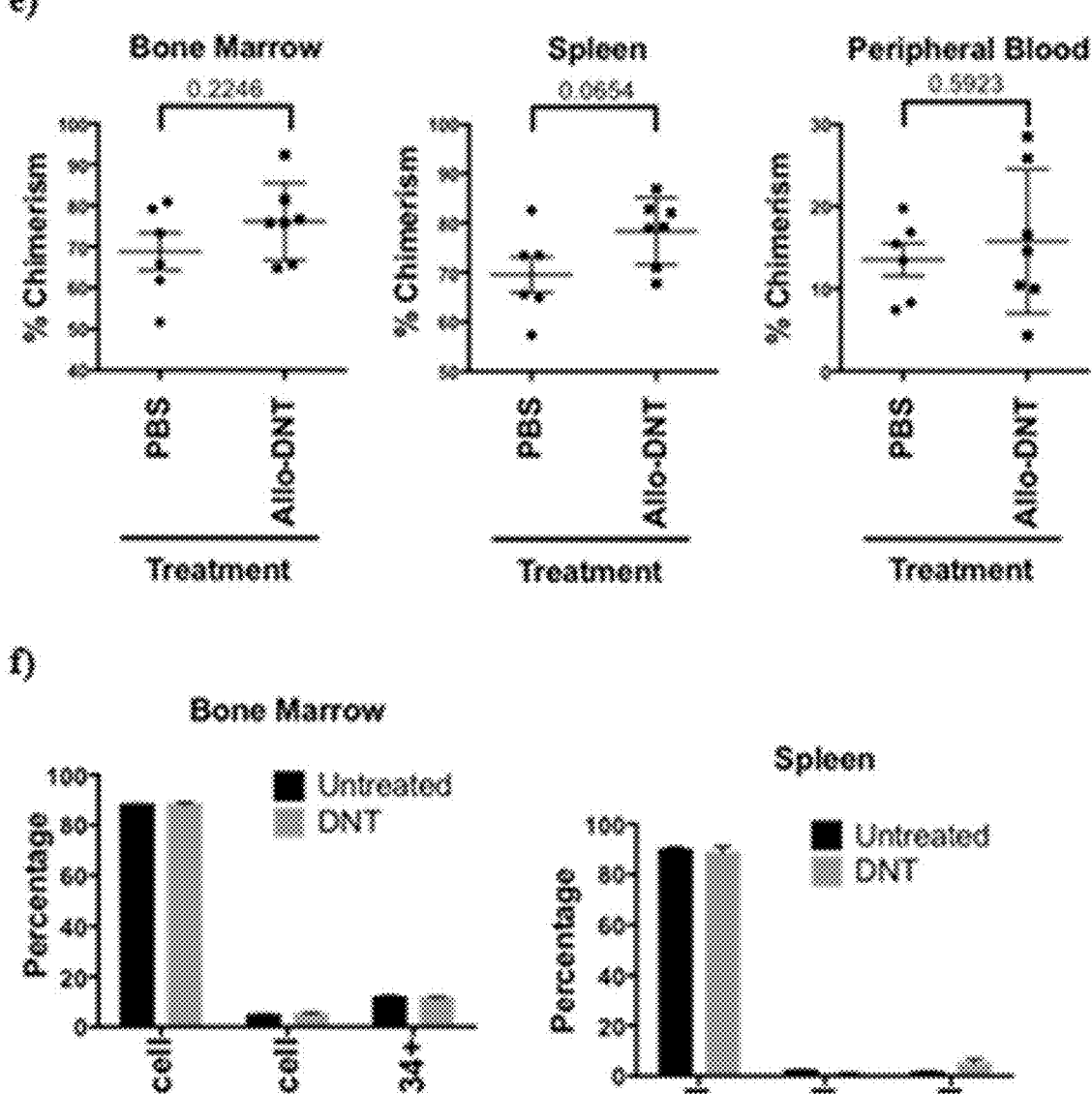

To further assess the potential effect of DNTs on normal hematopoietic cell differentiation and on mature hematopoietic cells in vivo, NSG mice were injected with normal HSPCs, and eight weeks later, mice were treated with DNTs or PBS. The engraftment frequency and the differentiation of human hematopoietic cells into different lineages were then compared between the two groups. Both the frequency (FIG. 9e) and the lineage composition (FIG. 9f) of human hematopoietic cells were comparable between DNT- and PBS-treated groups in PB, spleen and BM, indicating that DNTs do not alter the differentiation of hematopoietic cells in vivo. Moreover, the frequency of HSPC enriched CD34$^+$ cells in BM (FIG. 9f) was similar between the two treatment groups, further supporting the notion that ex vivo expanded allogenic DNTs do not target normal HSPCs. Taken together, these data indicate that DNTs are not cytotoxic to normal BM cells nor affect healthy donor stem cell engraftment or differentiation in xenograft models. These findings, for the first time, point to the safety and potential efficacy of ex vivo expanded DNTs as a novel immunotherapy to treat AML patients in chemotherapy-induced remission to decrease disease relapse and increase patient survival.

Therapeutic Indications

In view of the above examples, applications in the human context are expected to be validated, and include without limitation, the following.

To prevent or treat GVHD, e.g. when a patient is undergoing treatment for a disease where stem cell transplant is useful (e.g. for multiple Myeloma, . . . etc.), the patient could be provided DN Tregs subsequent to a stem cell or a cord blood cell transplant. This can be advantageous as it is after ablation of the patient's immune system. Alternatively or in combination, the patient could be provided DN Tregs prior to the stem cell or cord blood cell transplant. The DN Tregs administered could be allogenic or autologous.

To prevent or treat GVHD with leukemia, where stem cell and/or cord blood transplant forms a part of the treatment, the patient could be provided DN Tregs after chemotherapy/radiation treatment (for antileukemic effect). Alternatively or in combination, the patient could be provided DN Tregs after induction chemotherapy/radiation treatment and before stem cell or cord blood cell transplant (preferably after ablation of patient's own immune system). Alternatively or in combination, the patient could be provided DN Tregs after or concurrently with stem cell/cord blood transplant. Again, the DN Tregs administered could be allogenic or autologous.

Given the examples provided, it is expected that αβ-TCR$^{+-}$ and γδ-TCR+ DN Tregs would be useful in these human indications.

Although preferred embodiments of the invention have been described herein, it will be understood by those skilled in the art that variations may be made thereto without departing from the spirit of the invention or the scope of the appended claims. All documents disclosed herein, including those in the following reference list, are incorporated by reference.

REFERENCES

1. Wood K J, Bushell A, Hester J. Regulatory immune cells in transplantation. *Nat Rev Immunol* 2012, 12(6): 417-430.
2. McMurchy A N, Bushell A, Levings M K, Wood K J. Moving to tolerance: clinical application of T regulatory cells. *SeminImmunol* 2011, 23(4): 304-313.
3. Tang Q, Bluestone J A. Regulatory T-cell therapy in transplantation: moving to the clinic. *Cold Spring Harb Perspect Med;* 2013.
4. von Boehmer H, Daniel C. Therapeutic opportunities for manipulating Treg cells in autoimmunity and cancer. *Nat Rev Drug Discov* 2013, 12:51-63.
5. Curiel T J. Tregs and rethinking cancer immunotherapy. *J Clin Invest* 2007, 115(5):1167-1174.
6. Trzonkowski P, Dukat-Mazurek A, Bieniaszewska A, Marek-Trzonkowska N et al. Treatment of graft-vs-host disease with naturally occurring T regulatory cells. *BioDrugs* 2013, 27(6):605-614.
7. Veiga-Parga T, Sehrawat S, Rouse BT. Role of regulatory T cells during virus infection. *Immunol Rev* 2013, 255(1):182-196.
8. Toda A, Piccirillo C A. Development and function of naturally occurring CD4+CD25+ regulatory T cells. *J Leukoc Biol* 2006, 80(3): 458-470.
9. Sakaguchi S, Yamaguchi T, Nomura T, Ono M. Regulatory T cells and immune tolerance. *Cell* 2008, 133(5): 775-787.
10. Fischer K, Voelkl S, Heymann J, Przybylski G K, Mondal K, Laumer M, et al. Isolation and characterization of human antigen-specific TCR alpha beta+ CD4(–)CD8– double-negative regulatory T cells. *Blood* 2005, 105(7): 2828-2835.
11. Zhang Z X, Yang L, Young K J, DuTemple B, Zhang L. Identification of a previously unknown antigen-specific regulatory T cell and its mechanism of suppression. *Nature Medicin* 2000, 6(7): 782-789.
12. Ford M S, Young K J, Zhang Z X, Ohashi P S, Zhang L. The immune regulatory function of lymphoproliferative double negative T cells in vitro and in vivo. *J. Exp. Med.* 2002, 196(2): 261-267.

13. Chen W H, Diao J, Stepkowski S M, Zhang L. Both infiltrating regulatory T cells and insufficient antigen presentation are involved in long-term cardiac xenograft survival. *Immunol.*, 2007, 179(3): 1542-1548.

14. Chen W H, Zhou D J, Torrealba J R, Waddell T K, Grant D, Zhang L. Donor lymphocyte infusion induces long-term donor-specific cardiac xenograft survival through activation of recipient double-negative regulatory T cells. *J. Immunol.* 2005, 175(5): 3409-3416.

15. Zhang D, Yang W, Degauque N, Tian Y, Mikita A, Zheng X X. New differentiation pathway for double-negative regulatory T cells that regulates the magnitude of immune responses. *Blood* 2007, 109(9): 4071-4079.

16. Chen W, Ford M S, Young K J, Zhang L. Infusion of in vitro-generated DN T regulatory cells induces permanent cardiac allograft survival in mice. *Transplant Proceedings* 2003, 35(7): 2479-2480.

17. Lee B P, Mansfield E, Hsieh S C, Hernandez-Boussard T, Chen W, Thomson C W, et al. Expression profiling of murine double-negative regulatory T cells suggest mechanisms for prolonged cardiac allograft survival. *J Immunol* 2005, 174(8): 4535-4544.

18. Young K J, DuTemple B, Zhang Z X, Levy G A, Zhang L. CD4-CD8- regulatory T cells implicated in preventing graft-versus-host and promoting graft-versus-leukemia responses. *Transplant Proc* 2001, 33: 1762-1763.

19. Young K J, DuTemple B, Phillips M J, Zhang L. Inhibition of graft-versus-host disease by double-negative regulatory T cells. *J Immunol* 2003, 171(1): 134-141.

20. Juvet S C, Han M, Vanama R, Joe B, Kim E Y, Zhao F L, et al. Autocrine IFNgamma controls the regulatory function of lymphoproliferative double negative T cells. *PLoSOne* 2012, 7(10): e47732.

21. He K M, Ma Y, Wang S, Min W P, Zhong R, Jevnikar A, et al. Donor double-negative Treg promote allogeneic mixed chimerism and tolerance. *Eur J Immunol* 2007, 37(12): 3455-3466.

22. Ford M S, Chen W, Wong S, Li C, Vanama R, Elford A R, et al. Peptide-activated double-negative T cells can prevent autoimmune type-1 diabetes development. *Eur J Immunol* 2007, 37(8): 2234-2241.

23. Priatel J J, Utting O, Teh H S. TCR/Self-Antigen Interactions Drive Double-Negative T Cell Peripheral Expansion and Differentiation into Suppressor Cells. *J Immunol* 2001, 167(11): 6188-6194.

24. Hillhouse E E, Lesage S. A comprehensive review of the phenotype and function of antigen-specific immunoregulatory double negative T cells. *J Autoimmun* 2013, 40: 58-65.

25. Yanaba K, Bouaziz J D, Matsushita T, Tsubata T, Tedder T F. The development and function of regulatory B cells expressing IL-10 (B10 cells) requires antigen receptor diversity and TLR signals. *J. Immunol* 2009, 182(12): 7459-7472.

26. McIver Z, Serio B, Dunbar A, O'Keefe C L, Powers J, Wlodarski M, et al. Double-negative regulatory T cells induce allotolerance when expanded after allogeneic haematopoietic stem cell transplantation. *Br J Haematol* 2008, 141(2): 170-178.

27. Ye H, Chang Y, Zhao X, Huang X. Characterization of CD3+CD4-CD8- (double negative) T cells reconstitution in patients following hematopoietic stem-cell transplantation. *Transplant immunology* 2011, 25(4): 180-186.

28. Hippen K L, Merkel S C, Schirm D K, Sieben C M, Sumstad D, Kadidlo D M, et al. Massive ex vivo expansion of human natural regulatory T cells (T(regs)) with minimal loss of in vivo functional activity. *Science Translational Medicine* 2011, 3(83): 83ra41.

29. Butler M O, Imataki O, Yamashita Y, Tanaka M, Ansen S, Berezovskaya A, et al. Ex vivo expansion of human CD8+ T cells using autologous CD4+ T cell help. *PLoS One* 2012, 7(1): e30229.

30. Dienstmann R, Rodon J, Serra V, Tabernero J. Picking the point of inhibition: a comparative review of PI3K/AKT/mTOR pathway inhibitors. *Mol Cancer Ther.* 2014; 13(5):1021-31.

31. Allgauer A, Schreiner E, Ferrazzi F, Ekici A B, Gerbitz A, Mackensen A, et al. IL-7 Abrogates the Immunosuppressive Function of Human Double-Negative T Cells by Activating Akt/mTOR Signaling. Journal of immunology. 2015; 195(7):3139-48.

32. Fischer K, Voelkl S, Heymann J, Przybylski G K, Mondal K, Laumer M, et al. Isolation and characterization of human antigen-specific TCR alpha beta+CD4(-)CD8-double-negative regulatory T cells. Blood. 2005; 105(7): 2828-35.

33. Voelkl S, Gary R, Mackensen A. Characterization of the immunoregulatory function of human TCR-alphabeta+ CD4- CD8- double-negative T cells. European journal of immunology. 2011; 41(3):739-48.

34. Dienstmann R, Rodon J, Serra V, Tabernero J. Picking the point of inhibition: a comparative review of PI3K/AKT/mTOR pathway inhibitors. Mol Cancer Ther. 2014; 13(5):1021-31.

35. Shan J, Feng L, Li Y, Sun G, Chen X, Chen P. The effects of rapamycin on regulatory T cells: its potential time-dependent role in inducing transplant tolerance. Immunol Lett. 2014; 162(1 Pt A):74-86.

36. Merims S, Li X, Joe B, Dokouhaki P, Han M, Childs R W, et al. Anti-leukemia effect of ex vivo expanded DNT cells from AML patients: a potential novel autologous T-cell adoptive immunotherapy. Leukemia. 2011; 25(9): 1415-22.

S1. J. J. Cornelissen et al., Results of a HOVON/SAKK donor versus no-donor analysis of myeloablative HLA-identical sibling stem cell transplantation in first remission acute myeloid leukemia in young and middle-aged adults: benefits for whom? Blood 109, 3658-3666 (2007).

S2. C. Schmid et al., Outcome of patients with distinct molecular genotypes and cytogenetically normal AML after allogeneic transplantation. Blood 126, 2062-2069 (2015).

S3. A. D. Chantry et al., Long-term outcomes of myeloablation and autologous transplantation of relapsed acute myeloid leukemia in second remission: a British Society of Blood and Marrow Transplantation registry study. Biology of blood and marrow transplantation: journal of the American Society for Blood and Marrow Transplantation 12, 1310-1317 (2006).

S4. E. Brissot, M. Mohty, Which Acute Myeloid Leukemia Patients Should Be Offered Transplantation? Semin Hematol 52, 223-231 (2015).

S5. P. Vyas, F. R. Appelbaum, C. Craddock, Reprint of: Allogeneic hematopoietic cell transplantation for acute myeloid leukemia. Biol Blood Marrow Transplant 21, S3-10 (2015).

S6. K. Vincent, D. C. Roy, C. Perreault, Next-generation leukemia immunotherapy. Blood 118, 2951-2959 (2011).

S7. J. J. Cornelissen et al., The European LeukemiaNet AML Working Party consensus statement on allogeneic HSCT for patients with AML in remission: an integrated-risk adapted approach. Nat Rev Clin Oncol 9, 579-590 (2012).

S8. D. Araki et al., Allogeneic Hematopoietic Cell Transplantation for Acute Myeloid Leukemia: Time to Move Toward a Minimal Residual Disease-Based Definition of Complete Remission? Journal of clinical oncology: official journal of the American Society of Clinical Oncology 34, 329-336 (2016).

S9. M. M. Horowitz et al., Graft-versus-leukemia reactions after bone marrow transplantation. Blood 75, 555-562 (1990).

S10. P. L. Weiden et al., Antileukemic effect of graft-versus-host disease in human recipients of allogeneic-marrow grafts. The New England journal of medicine 300, 1068-1073 (1979).

S11. M. R. van den Brink et al., Relapse after allogeneic hematopoietic cell therapy. Biol Blood Marrow Transplant 16, S138-145 (2010).

S12. A. Montero et al., T-cell depleted peripheral blood stem cell allotransplantation with T-cell add-back for patients with hematological malignancies: effect of chronic GVHD on outcome. Biol Blood Marrow Transplant 12, 1318-1325 (2006).

S13. T. A. Gooley et al., Reduced mortality after allogeneic hematopoietic-cell transplantation. The New England journal of medicine 363, 2091-2101 (2010).

S14. R. Champlin et al., Harnessing graft-versus-malignancy: non-myeloablative preparative regimens for allogeneic haematopoietic transplantation, an evolving strategy for adoptive immunotherapy. British journal of haematology 111, 18-29 (2000).

S15. J. Barrett, R. Childs, Non-myeloablative stem cell transplants. British journal of haematology 111, 6-17 (2000).

S16. M. Edinger et al., CD4+CD25+ regulatory T cells preserve graft-versus-tumor activity while inhibiting graft-versus-host disease after bone marrow transplantation. Nature medicine 9, 1144-1150 (2003).

S17. B. Sprangers, B. Van Wijmeersch, S. Fevery, M. Waer, A. D. Billiau, Experimental and clinical approaches for optimization of the graft-versus-leukemia effect. Nat Clin Pract Oncol 4, 404-414 (2007).

S18. P. Fontaine et al., Adoptive transfer of minor histocompatibility antigen-specific T lymphocytes eradicates leukemia cells without causing graft-versus-host disease. Nature medicine 7, 789-794 (2001).

S19. Z. X. Zhang, L. Yang, K. J. Young, B. DuTemple, L. Zhang, Identification of a previously unknown antigen-specific regulatory T cell and its mechanism of suppression. Nature medicine 6, 782-789 (2000).

S20. K. J. Young, B. DuTemple, M. J. Phillips, L. Zhang, Inhibition of graft-versus-host disease by double-negative regulatory T cells. Journal of immunology 171, 134-141 (2003).

S21. K. J. Young, B. DuTemple, Z. Zhang, G. Levy, L. Zhang, CD4(−)CD8(−) regulatory T cells implicated in preventing graft-versus-host and promoting graft-versus-leukemia responses. Transplantation proceedings 33, 1762-1763 (2001).

S22. S. C. Juvet et al., Autocrine IFNgamma controls the regulatory function of lymphoproliferative double negative T cells. PLoS one 7, e47732 (2012).

S23. K. M. He et al., Donor double-negative Treg promote allogeneic mixed chimerism and tolerance. Eur J Immunol 37, 3455-3466 (2007).

S24. K. J. Young, L. S. Kay, M. J. Phillips, L. Zhang, Antitumor activity mediated by double-negative T cells. Cancer Res 63, 8014-8021 (2003).

S25. Z. McIver et al., Double-negative regulatory T cells induce allotolerance when expanded after allogeneic haematopoietic stem cell transplantation. British journal of haematology 141, 170-178 (2008).

S26. H. Ye, Y. Chang, X. Zhao, X. Huang, Characterization of CD3+CD4-CD8− (double negative) T cells reconstitution in patients following hematopoietic stem-cell transplantation. Transplant immunology 25, 180-186 (2011).

S27. L. Covassin et al., Human peripheral blood CD4 T cell-engrafted non-obese diabetic-scid IL2rgamma(null) H2-Ab1 (tm1Gru) Tg (human leucocyte antigen D-related 4) mice: a mouse model of human allogeneic graft-versus-host disease. Clin Exp Immunol 166, 269-280 (2011).

S28. H. Fujii et al., Humanized Chronic Graft-versus-Host Disease in NOD-SCID il2rgamma−/− (NSG) Mice with G-CSF-Mobilized Peripheral Blood Mononuclear Cells following Cyclophosphamide and Total Body Irradiation. PLoS One 10, e0133216 (2015).

S29. R. S. van Rijn et al., A new xenograft model for graft-versus-host disease by intravenous transfer of human peripheral blood mononuclear cells in RAG2−/− gammac−/− double-mutant mice. Blood 102, 2522-2531 (2003).

What is claimed is:

1. A method of treating allograft rejection, graft vs. host disease (GVHD), or an autoimmune disease in a subject, comprising:

expanding human CD4⁻CD8⁻ regulatory T cells (DN Tregs) from a population of cells comprising DN Tregs, by:

depleting the population of cells comprising DN Tregs of CD4⁺ and CD8⁺ cells;

activating the depleted population of cells with anti-CD3 antibodies; then culturing the activated population of cells with artificial antigen presenting cells (APCs) that express at least one cell surface adhesion molecule for immunological synapse, the at least one cell surface adhesion molecule comprising at least one of CD54 and CD58;

wherein the DN Tregs are $\alpha\beta$-TCR⁺CD56⁻, $\gamma\delta$-TCR⁺, or both; and administering to the subject a therapeutically effective amount of the expanded DN Tregs.

2. The method of claim 1, for treating allograft rejection.

3. The method of claim 1, for treating GVHD.

4. The method of claim 1, for treating an autoimmune disease.

5. The method of claim 1, wherein the artificial APCs display anti-CD3 antibodies.

6. The method of claim 5, wherein the artificial APCs further express a co-stimulatory molecule.

7. The method of claim 6, wherein the co-stimulatory molecule is at least one of CD80, CD86, CD83, 4-1BBL, OX40L, ICOSL, CD40L, and CD28 antibody.

8. The method of claim 5, wherein the artificial APCs do not express inhibitory molecules.

9. The method of claim 5, wherein the artificial APCs further express at least one of M-CSF, IL-6, IL-8, TGF-$\beta$, MIP-1a, IL-7, IL-15 and IL-2.

10. The method of claim 1, wherein the artificial APCs are K-562 cells.

11. The method of claim 1, wherein the culturing is additionally in the presence of at least one of IL-2, IL-7 and IL15.

12. The method of claim 1, wherein the activating is with anti-CD3 antibodies cross-linked, or otherwise attached, to a surface.

13. The method of claim 1, wherein the activating is with soluble anti-CD3 antibodies.

14. The method of claim 1, wherein the activating is sequentially with anti-CD3 antibodies cross-linked, or otherwise attached, to a surface and soluble anti-CD3 antibodies.

15. The method of claim 1, wherein the population comprises peripheral blood mononuclear cells (PBMCs) or cord blood mononuclear cells (CMBCs).

16. The method of claim 1, further comprising incubating the expanded DN Tregs with at least one inhibitor of the PI3K/AKT/mTOR pathway prior to administration.

17. The method of claim 16, wherein the at least one inhibitor is a mTOR inhibitor, dual PI3K/mTOR inhibitor, AKT inhibitor, or Pan-class I and isoform-specific PI3K inhibitors.

18. The method of claim 16 wherein the inhibitor is a Rapalog.

19. The method of claim 16, wherein the inhibitor is rapamycin, deforolimus, emsirolimus, everolimus, ridaforolimus, temsirolimus or a mTORC1/mTORC2 dual inhibitor.

20. The method of claim 19, wherein the inhibitor is rapamycin.

21. The method of claim 16, wherein the inhibitor is Wortmannin, LY294002, PKI-179, or Akt inhibitor IV.

22. The method of claim 8, wherein the inhibitory molecule is PDL1, PDL2, B7H3, or B7H4.

23. The method of claim 1, wherein the artificial APC is an artificial APC:

i. expressing 4-1BBL and membrane-bound IL-15;
   ii. expressing CD64, CD86, 4-1BBL, truncated CD19, and membrane-bound IL-21;
   iii. expressing CD64 and CD86;
   iv. expressing HLA class I, CD80, and CD83;
   v. expressing CD64 and 4-1BBL;
   vi. expressing CD32, CD80, CD83, CD86, and 4-1BBL; or
   vii. expressing CD64, CD86, 4-1BBL, truncated CD19, and membrane-bound IL-15.

\* \* \* \* \*